Figure 1A:
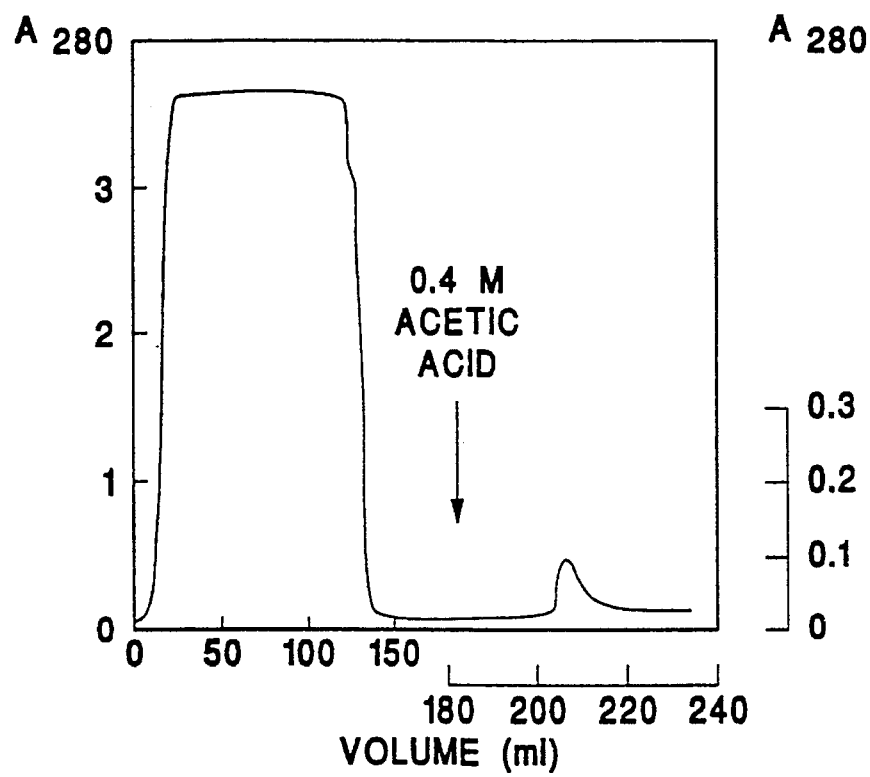

United States Patent [19]

Höök et al.

[11] Patent Number: 5,571,514
[45] Date of Patent: Nov. 5, 1996

[54] FIBRONECTIN BINDING PROTEIN AS WELL AS ITS PREPARATION

[75] Inventors: Magnus Höök, Birmingham, Ala.;
Martin K. Lindberg, Upsala, Sweden;
Lars C. Signäs, Upsala, Sweden;
Torkel M. Wadström, Lund, Sweden;
Gunnar Fröman, Upsala, Sweden

[73] Assignee: Alfa Laval AB, Tumba, Sweden

[21] Appl. No.: 259,000

[22] Filed: Jun. 13, 1994

Related U.S. Application Data

[62] Division of Ser. No. 7,817, Jan. 22, 1993, Pat. No. 5,320,951, which is a continuation of Ser. No. 201,028, Jun. 1, 1988, abandoned.

[30] Foreign Application Priority Data

Jun. 1, 1987 [SE] Sweden .................................. 8702272

[51] Int. Cl.$^6$ .................................................. A61K 39/085
[52] U.S. Cl. ........................................ 424/190.1; 424/243.1; 435/69.1; 435/69.3; 435/252.3; 435/320.1; 530/324

[58] Field of Search ............................. 424/190.1, 243.1, 424/278.1; 435/69.1, 252.3, 320.1, 69.3; 536/23.7; 530/350, 324

[56] References Cited

U.S. PATENT DOCUMENTS 5,320,951  6/1994  Höök et al. .......................... 435/69.1

OTHER PUBLICATIONS

Flock et al., Embo J. 6(8):2351–2357, 1987.
Ryden et al., J. Biol. Chem. 258(5):3396–3401, 1983.
Abrahmsen et al., Nucl. Acid. Res. 14: 7487–7500, 1986.
Lofdahl et al., Pnas, 80, 697–701, Feb. 1983.

Primary Examiner—Mary E. Mosher
Assistant Examiner—Laurie Scheiner
Attorney, Agent, or Firm—Burns, Doane, Swecker & Mathis

[57] ABSTRACT

The present invention relates to a new recombinant hybrid-DNA-molecule comprising nucleotide sequence from *S. aureus* coding for a protein, or polypeptide, having fibronectin binding properties.

8 Claims, 10 Drawing Sheets

Fig. 8A.1

Fig. 8A:2

FIBRONECTIN BINDING PROTEIN AS WELL AS ITS PREPARATION

DESCRIPTION

This application is a divisional, of application Ser. No. 08/007,817, filed Jan. 22, 1993, now U.S. Pat. No. 5,320,951, which is a continuation of application Ser. No. 07/201,028, filed Jun. 1, 1988, now abandoned.

TECHNICAL FIELD

The present invention relates to a fibronectin binding protein as well as hybrid-DNA-molecules, e.g. plasmids or phages comprising a nucleotide sequence coding for said protein. Further the invention relates to microorganisms comprising said molecules and their use producing said protein, as well as the synthetic preparation of said protein.

The object of the present invention is to obtain a minimal fibronectin binding protein.

A further object is to obtain said protein by means of a genetic engineering technique by using e.g. a plasmid comprising a nucleotide sequence coding for said protein.

A further object is to obtain a possibility of preparing said protein by chemical synthesis.

Further objects will be apparent from the following description.

BACKGROUND OF THE INVENTION

WO-A1-85/05553 discloses bacterial cell surface proteins having fibronectin, fibrinogen, collagen, and/or laminin binding ability. Thereby it is shown that different bacteria have an ability to bind to fibronectin, fibrinogen, collagen, and/or laminin. It is further shown that fibronectin binding protein has a molecular weight of 165 kD and/or 87 kD, whereby it is probable that the smaller protein is a part of the larger one.

Fibronectin is a large glycoprotein ($M_r$ ca 450 kd) with two similar subunits, which may vary in moleclar size depending on a complex splicing pattern of a precursor mRNA (1). The major function of fibronectin, which is found in body fluids, blood clots and extracellular matrices, seems to be related to the ability of the protein to mediate substrate adhesion of most eukaryotic cells (2, 3, 4, 5.)

In the late seventies, Kuusela found that fibronectin not only interacts with eucaryotic cells but also binds to cells of *Staphylococcus aureus* (6). Since this observation, a number of pathogenic microorganisms have been shown to bind to fibronectin with a high degree of specificity and a high (7). Fibronectin in the extracellular matrix appears to serve as a substratum also for the adhesion of different microorganism The binding of fibronectin may for some microorganisms represent a crucial step in the colonization of host tissue and development of infection.

Several different cell surface components have been implicated as fibronectin receptors on Gram-positive bacteria including lipotechioc acid (8, 9) and protein (10). In previous studies a fibronectin binding protein with a $M_r$ of 197–210 kD has been isolated from *S. aureus* strain Newman (11, 12) and tentatively identified as a fibronectin receptor. To further characterize this fibronectin binding protein from S aureus, the gene for this protein has been cloned in *E. coli*. The fibronectin binding domain with in this protein has also been localized and the behaviour of a fusin protein containing this domain and IgG-binding regions of protein A will be disclosed below.

DESCRIPTION OF THE INVENTION

It has now surprisingly been found possible to obtain a hybride-DNA-molecule comprising a nucleotide sequence coding for a protein or a polypeptide having fibronectin binding properties. As evident from below the following nucleotide sequence [SEQ ID NO. 4] is present in the gene coding for said protein:

```
GGC CAA AAT AGC GGT AAC CAG TCA TTC GAG GAA GAC ACA GAA GAA

GAC AAA CCT AAA TAT GAA CAA GGT GGC AAT ATC GTA GAT ATC GAT

TTT GAT AGT GTA CCT CAA ATT CAT GGT CAA AAT AAA GGT AAT CAG

TCA TTC GAG GAA GAT ACA GAA AAA GAC AAA CCT AAG TAT GAA CAT

GGC GGT AAC ATC ATT GAT ATC GAC TTC GAC AGT GTG CCA CAT ATT

CAC GGA TTC AAT AAG CAC ACT GAA ATT ATT GAA GAA GAT ACA AAT

AAA GAT AAA CCA AGT TAT CAA TTC GGT GGA CAC AAT AGT GTT GAC

TTT GAA GAA GAT ACA CTT CCA AAA GTA AGC GGC CAA AAT GAA GGT

CAA CAA AGC ATT GAA GAA GAT ACA ACA CCT CCA ATC GTG CCA CCA

ACG CCA CCG ACA CCA GAA GTA CCA AGT GAG CCG GAA ACA CCA ACG

CCA CCA ACA CCA GAA GTA CCA AGT GAG CCG GAA ACA CCA ACA CCA

CCG ACA CCA GAA GTG CCG AGT GAG CCA GAA ACT CCA ACA CCG CCA

ACA CCA GAG GTA CCA GCT
```

The invention further comprises a plasmid or phage comprising a nucleotide sequence coding for said fibronectin binding protein.

The invention further comprises a microorganism comprising at least one hybrid-DNA-molecule according to the above.

The invention further comprises a method for producing a fibronectin binding protein whereby at least one hybrid-DNA-molecule of above is introduced into a microorganism, cultivating said microorganism in a growth medium, and isolating the protein thus formed by means of an affinity chromatography on a fibronectin bound to an insolubilized carrier followed by ion exchange chromatography.

A further aspect of the invention comprises a chemical synthesis of the fibronectin binding protein, whereby an amino acid sequence is built up based on said nucleotide sequence encoding for said protein starting from the C-terminal histidine which is stepwise reacted with the appropriate amino acid, whereby it is finally reacted with glycine at the N-terminal end, to form the fibronectin binding peptide region.

Appropriate carrier proteins can be coupled to the amino acid sequence as well, such as IgG binding regions of protein A.

The invention will be described in the following with reference to the examples given, however, without being restricted thereto.

EXAMPLE 1

Screening of a Gene Bank For Fibronectin Binding Protein (FNBP)

A gene bank in plasmid pBR322 of chromosomal DNA from *Staphylococcus aureus* strain 8325-4 earlier described by (13) was screened for clones expressing FNBP. *E. coli* clones were lysed and the lysates were testeo for their ability to inhibit the of $^{125}$I-fibronectin to cells of *S. aureus* Cowan I as described in the method section. To simplify screening the clones were pooled in lots of 25, lysed and tested. Out of the 22 pools tested, the one with the highest inhibitory activity was retested in 5 pools of 5. Finally, the individual clones in one positive pool were tested resulting in the isolation of one single positive clone. The plasmid in the positive clone was called pFR001.

This plasmid pFR001 in an *E. coli* strain 259 has been deposited at the Deutsche Sammlung von Mikroorganismen (DSM) and has thereby been allocated the deposition number 4124.

Isolation of the Staphylococcal Fnbp From *E. Coli* pFR001

The *E.coli* clone, positive for FNBP, was grown in LB-medium at 37° C. to the stationary growth phase. The bacterial cells were centrifuged and lysed by an osmotic shock procedure (14). To exclude that inhibitory effect of the shock lysate on the binding of $^{125}$I-fibronectin to *S. aureus* cells is due to proteolytic activity, lysate was added to the incubation mixture and the amount of $^{125}$I-fibronectin bound to *S. aureus* was determined after 1,2,3, and 4 hrs of incubation. Throughout this incubation period, the level of inhibition caused by the lysate remained constant (e.g. 50%) suggesting that the observed inhibition was not due to a progressive degradation of the $^{125}$I-labelled ligand or corresponding receptor.

Figure 1B:
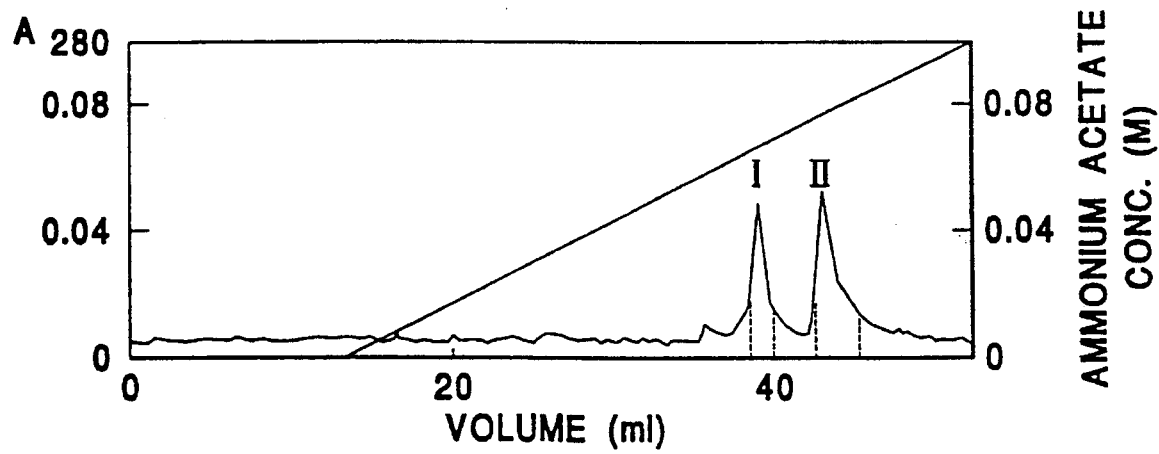
Figure 2:
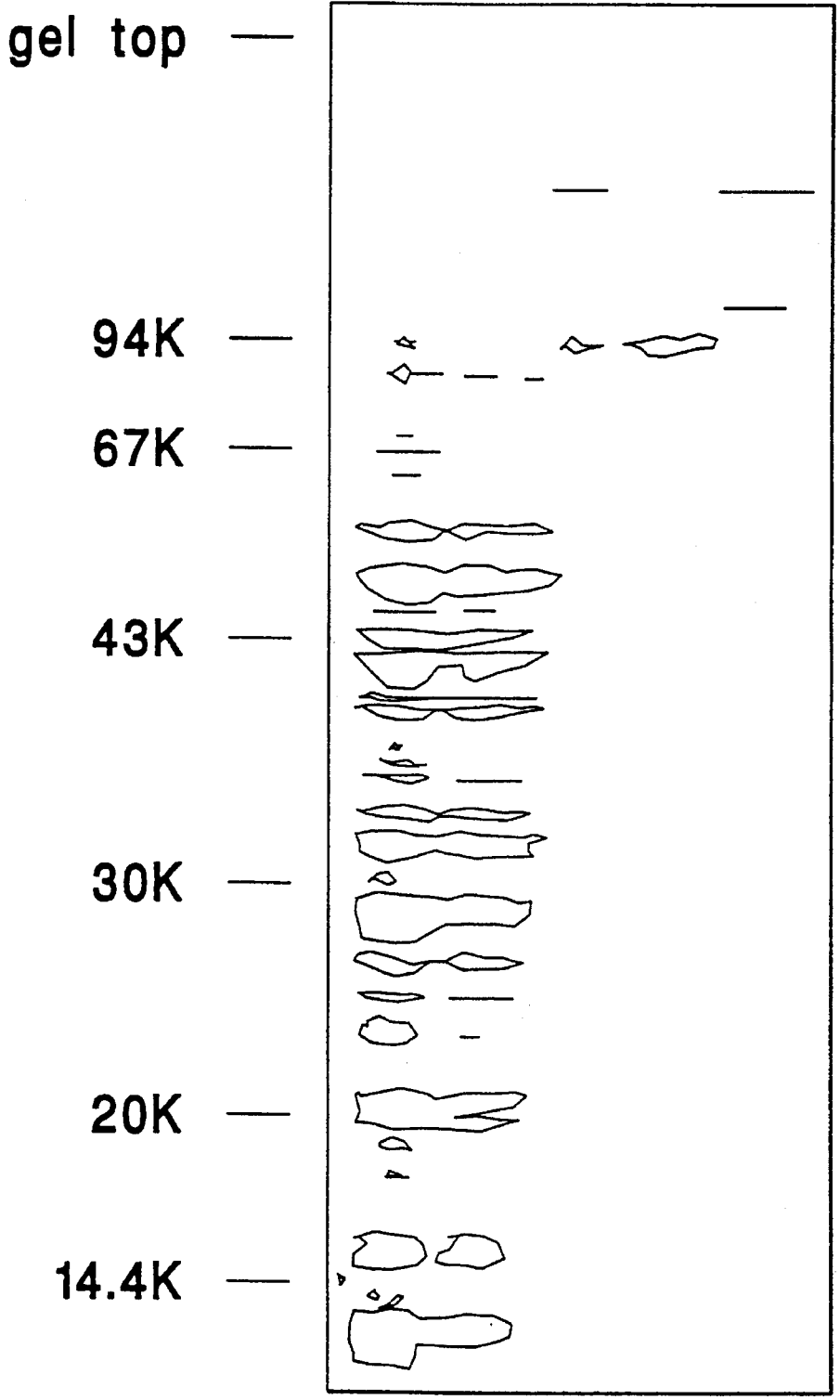

If the inhibitory activity is due to the presence of FNBP-like structures in the lysate, these should express a specific affinity for fibronectin. The lysate, was therefore analysed by affinity chromatography on a column of fibronectin-Sepharose as described in Materials and Methods (FIG. 1A). The purification was about 30 fold. Further fractionation was achieved by subjecting the affinity purified material to ion-exchange chromatography using a mono Q column fitted on to a FPLC-system. In this fractionation step two major peaks were obtained (FIG. 1B). Analyses by polyacrylamide gel electrophoresis indicated th at the two peaks contained proteins of molecular weights 165 and 87 kD, respectively (FIG. 2). Both components inhibited the binding of $^{125}$I-fibronectin to *S. aureus*. The fraction containing the 165 kD protein had a specific inhibitory activity of 220 units/qg representing a 430-fold purification from the original shock lysate and it was 30 times more active than the 87 kD protein on a molar basis (data not shown).

Amino acid analysis of the two proteins showed that they had a very similar amino acid composition which also closely resembled that determined for the native FNBP isolated from *S. aureus* strain Newman (Table 1). The immuological relationship of 165 kD protein isolated from *E.coli* pFR001 to the native FNBP isolated from *S. aureus* strain Newman was analyzed. The 165 kD protein was $^{125}$I-labelled and immunoprecipitaited with increasing dilutions of an antibody to *S. aureus* strain Newman. A 300-fold dilution of the antiserum precipitatd 50% of the $^{125}$I-labelled protein. Unlabelled 165 and 87 kD proteins well as the native FNBP interferred with the immunoprecipitation of the labelled 165 kD protein (data not shown). These observations suggest that the 165 and 87 kD proteins isolated from *S. aureus* strain Newman are closely related to fibronectin binding protein (FNBP).

Identification of The Region of The Fnbp-Gene Coding for The Binding Activity

The size of the insert in plasmid pFR001 is about 6.5 kbp. The restriction map of the insert is shown in FIG. 3(A). In order to determine the transcription direction and to localize the region coding for the binding function, the PstI fragment of about 3.7 kbp was recloned in the PstI site of pBR322. This results in loss of the ampicillin resistance phenotype conferred by this plasmid. Eight such clones were obtained, five of which were positive and three negative for fibronectin binding activity. One of each was tested for the orientation of the PstI fragment. The plasmid of the positive clone pFR004 had the EcoRI site closest to the Amp-promoter and that of the negative clone had the reverse orientation. These data indicated that the transcription orientation is from EcoRI to PstI on the 3.7 kbp EcoRI-PstI fragment and that at least a part of the fnbp-gene, which codes for the binding function, is located on this fragment. To verify this, the Amp-promoter in pFR004 was removed by EcoRI digestion followed by religation of the plasmid. The resulting plasmid pFR008 does not express fibronectin binding activity. In pFR001 the endogenous promoter is thus presumably located somewhere on the left hand side of the EcoRI site as indicated by the arrow in FIG. 3A). By a plasmid construction (not described in detail here) the EcoRI (in the insert)-SalI (in pBR322) fragment from pFR001 was introduced into pFR008. The fibronectin binding activity was then regained, due to the restoration of the endogenous promoter from the fnbp-gene.

Knowing the transcription direction of the fnbp-gene (from left to right as drawn in FIG. 3(A)) fusions were made to the gene for staphylococcal protein A. An expression/secretion vector called pRIT3 based on the protein A gene with restriction enzyme multilinker has been constructed (15). The multi-linker is placed immediately downstream of the last IgG-binding region, thus eliminating the C-terminal cellwall binding region of protein A. The 3.7 kbp EcoRI-PstI fragment from pFR001 was inserted into this vector expecting it to, encode a protein A-FNBP fusion protein, providing the reading frame was correct. This was obviously the case since the clone containing this plasmid, called pFR013, is positive in tests for both protein A and FNBP.

Plasmid pFR013 was treated with exonuclease Bal31 in order to identify a region smaller than the 3.7 kbp insert coding for the fibronectin binding activity. The plasmid was cleaved with EcoRI or PstI (at the 5' and the 3' end of the coding region, respectively), treated for various times with Bal31 and religated. During ligations a 20-fold excess of an EcoRI linker was added in oder to introduce EcoRI sites at new positions. FIG. 3(C) shows the deletions obtained from either the 3' or the 5' end and the corresponding fibronectin binding activity. A region of the gene of about 700 bp coding for binding activity is located between the end points of deletions number 56 (deletion from the 5 end) and number 22 (deletion from the 3 end). From deletion plasmid number 56, the 900 bp region from the newly introduced EcoRI site to the PvuII site was subcloned. This fragment was cloned into pUC18 cleaved with EcoRI and SmaI. The resulting plasmid, which encodes a fusion protein with both β-galactosidase and fibronectin binding activity, is called pFR015. The fragment can be recloned from pFR015 by EcoRI and BamHI cleavages because of the multilinker in pUC18.

Restriction fragments were also subcloned as indicated in FIG. 3(B). In the case of EcoRI-PstI and EcoRI-ClaI fragments the protein A expression vector pRIT3 was used. Fragments BalI-PvuII and BalI-HincII were subcloned and expressed in pUC18. In all cases, except for the EcoRI-ClaI fragment, fusion proteins with fibronectin binding activity were obtained. The negative result in the case of the ClaI-ClaI subclone may be due to the insert appearing in the wrong reading frame.

Production and Characterization of a Fusion Protein, ZZ-FR

The yield of the 165 kD protein (FIG. 2) from an osmotic shock lysate of E. coli HB101 cells carrying the plasmid pFR001 was approximately 40/μg per liter culture medium. Even if there were losses due to degradation of the high molecular weight compound during the purification all data indicated that the fnbp-gene with the endogenous promoter is weakly expressed in E. coli. In order to improve the level of expression we used a recently developed expression system, which allows heterologous proteins to be secreted to the growth medium of E. coli (16). The plasmid vector used, pEZZ318, contains two synthetic slightly modified IgG-binding domains of the gene for staphylococcal protein A preceeded by the promoter and signal sequence of the same gene. A BalI-PvuII fragment of approximately 600 bp of the fnbp-gene (FIG. 3(B)) cloned in pUC18 was recloned into pEZZ318 cleaved with EcoRI and HindIII. After ligation and transformation pEZZ-FR was isolated. This plasmid encodes a fusion protein consisting of the IgG binding product ZZ and fibronectin binding region FR of the FNBP.

For production of the ZZ-FR protein E. coli strain HB101 carrying the plasmid pEZZ-FR was grown overnight in Trypticase Soy Broth. Bacteria were removed by centrifugation and the growth medium was passed through an IgG-Sepharose Fast Flow column. After washing the column with TST-buffer (50 mM Tris-HCl pH 7.4 150 mM NaCl, 0,05% Tween$^R$ 20) the ZZ-FR protein was eluted with 0,5 M acetic acid titrated to pH 2.8 using ammonium acetate. Approximately 50 mg protein was eluted from the column per liter of growth medium applied.

Figure 4:
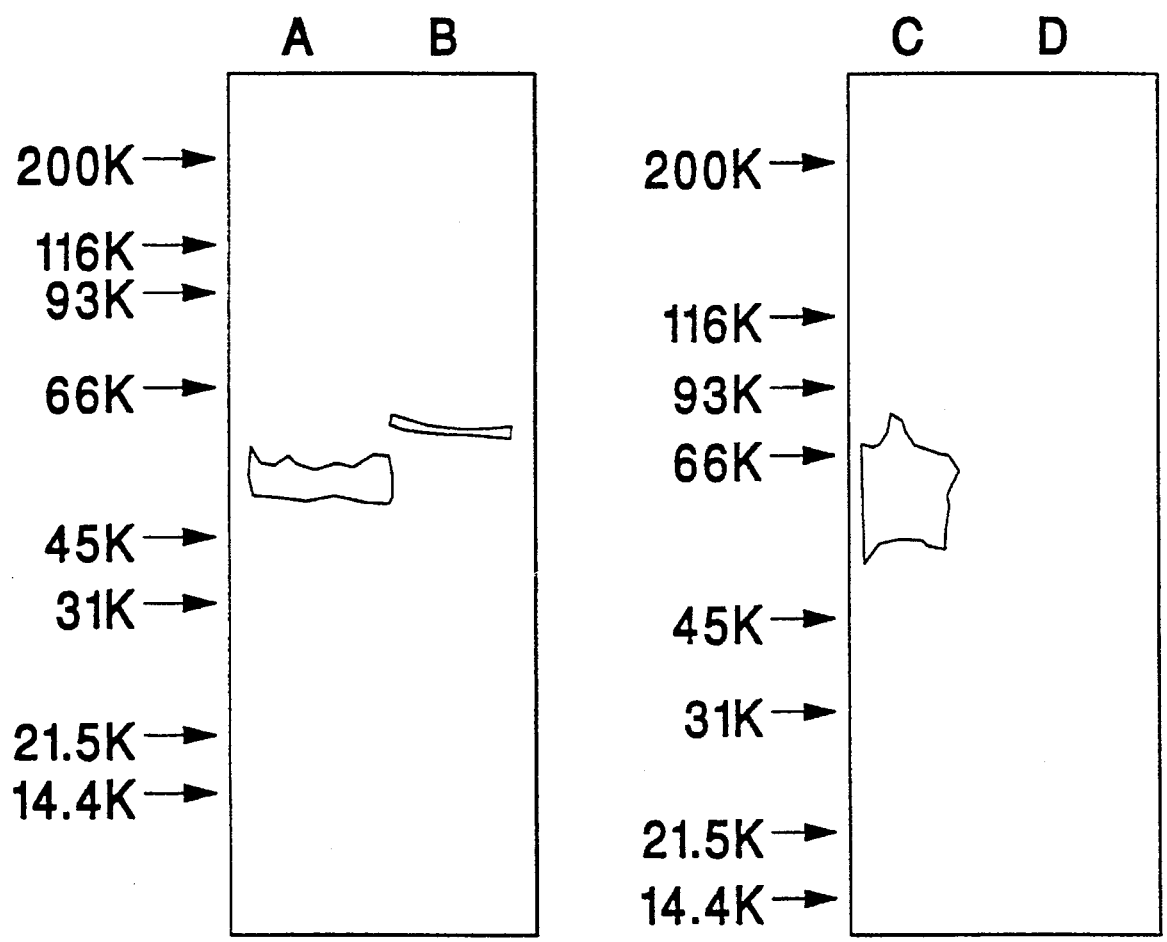

After lyophilization the eluted material was analyzed by SDS-PAGE, which revealed a major protein band at approximately 63 kD (FIG. 4). In addition, bands corresponding to smaller fragments appeared, probably due to proteolytic degradation of the fusion protein. The intact protein A which was run on the same gel appeared as a diffuse band around 56 kD. The proteins in the gel were electrophoretically transferred to a nitrocellulose paper and probed with a $^{125}$I-labelled 29 kD fibronectin fragment. FIG. 4, lanes C and D, shows that the fusion protein but not intact protein A, binds the radiolabelled fibronectin fragment.

Further evidence for the fibronectin binding ability of the ZZ-FR fusion protein was obtained by affinity chromatography on a Sepharose column substituted with the 29 kD fibronectin fragment. The fusion protein was bound to the column and was eluted from the affinity matrix with 6M GuHCl (FIG. 5A). The fibronectin binding activity of the ZZ-FR fusion protein was apparently located in the FR-region since intact protein A did not bind to the affinity matrix (FIG. 5B). The portion of the ZZ-FR fusion protein preparation that did not bind to the affinity matrix consisted of proteins with $M_R$ lower than of the intact fusion protein (FIG. 6, lane A) whereas the material binding to the column consisted of an almost pure preparation of intact 63 kD ZZ-FR fusion protein (FIG. 6, lane B).

Figure 7:
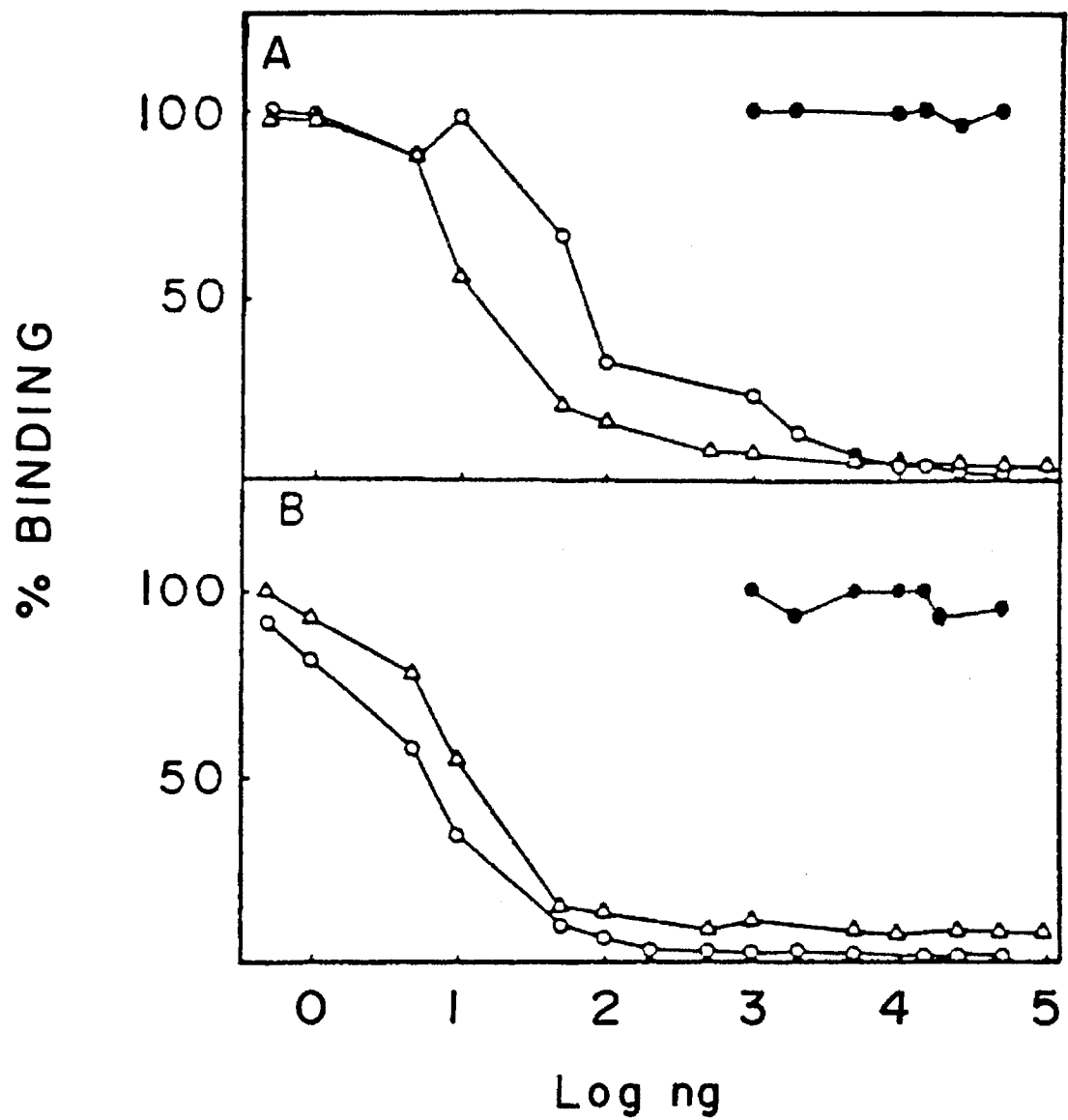

In oder to determine how much of the fibronectin binding capacity of staphylocaccal cells that can be ascribed to the cloned FNBP, the inhibitory activity of the fusion protein ZZ-FR was quantified. As shown in FIG. 7 the fusion protein totally inhibited the binding of $^{125}$I-labelled 29 kD fragment as well as intact fibronectin to cells of both S. aureus strains Newman and 8325-4, protein A, which was used as a control, did not inhibit the binding (FIG. 7).

After the report by Kuusela (6) that S. aureus binds to fibronectin much work has been focused on attempts to identify the bacterial component(s) responsible for the binding. The rationale for these studies has been that binding of pathogenic bacteria to fibronectin may represent a mechanism of tissue adherence of crucial importance in the early stages of an infection. Proteins purified by affinity chromatography on immobilized fibronectin, have been implicated in the binding of staphylococcal cells to fibronectin. However the reported lecular weights of the fibronectin binding proteins vary from 18 kD (10) all the way up to 197 and 210 kD (11, 17). The main reason for the heterogeniety in molecular size may be proteolytic degradation of the proteins during the isolation procedures.

In the present disclosure the cloning in E. coli of a gene coding for a fibronectin binding protein from S. aureus strain 8325-4 is disclosed. When the fnbp-gene is expressed in E. coli from the endogenous promoter the protein can be isolated from the periplasm by osmotic shock. This indicates that not only the promoter but also the signal peptide is functional in E. coli.

Although the proteins coded for by the cloned fnbp-gene have molecular weights of 165 and 87 kD (FIG. 2), which is smaller than the FNBP isolated from S. aureus strain Newman ($M_R$=210 kD) (12), their amino acid compositions closely resemble that of the native protein (Table 1). Furthermore, antibodies raised against the native FNBP cross-react with the 165 and 87 kD proteins. These data strongly suggest that the structure of the proteins coded for by the cloned gene from S. aureus strain 8325-4 resembles that of native FNBP from S. aureus strain Newman. The 87 kD protein may be the result of pretermination at the transcriptional or translational level or alternatively proteolytic cleavage of the 165 kD protein. At present it cannot be explained why the 165 kD protein is as much as 30 times more active than the 87 kD protein in inhibition of fibronectin binding to S. aureus cells.

By deletion mapping using Bal31-clevage and subcloning of restriction fragments the domain of the fnbp-gene encoding the fibronectin binding activity had been located to a region of approximately 350 bp (FIG. 3(B)). A fragment of the gene of approximately 600 bp covering these 350 bp was ligated directly to a tandemly repeated sequence (zz) of a synthetic IgG-binding domain of the protein A gene preceeded by the protein A promoter and signal sequence in expression vector pEZZ318 (16). The resulting fusion protein (ZZ-FR), which has a molecular weight of approximately 63 kD as determined by SDS-PAGE (FIG. 4), contains 126 amino acids of the ZZ domain followed by approximately 200 amino acids encoded by the 600 bp insert from the fnbp-gene The C-terminal end of the protein consists of amino acids which are the result of an out of frame read-through into the lacZ' gene of the vector until a translation stop codon is reached. The fusion protein (ZZ-FR), which is expressed at a high level and secreted to the growth medium of E. coli, is easily isolated by affinity chromatogtaphy making use of the IgG-binding ability of the ZZ-domain.

Figure 5:
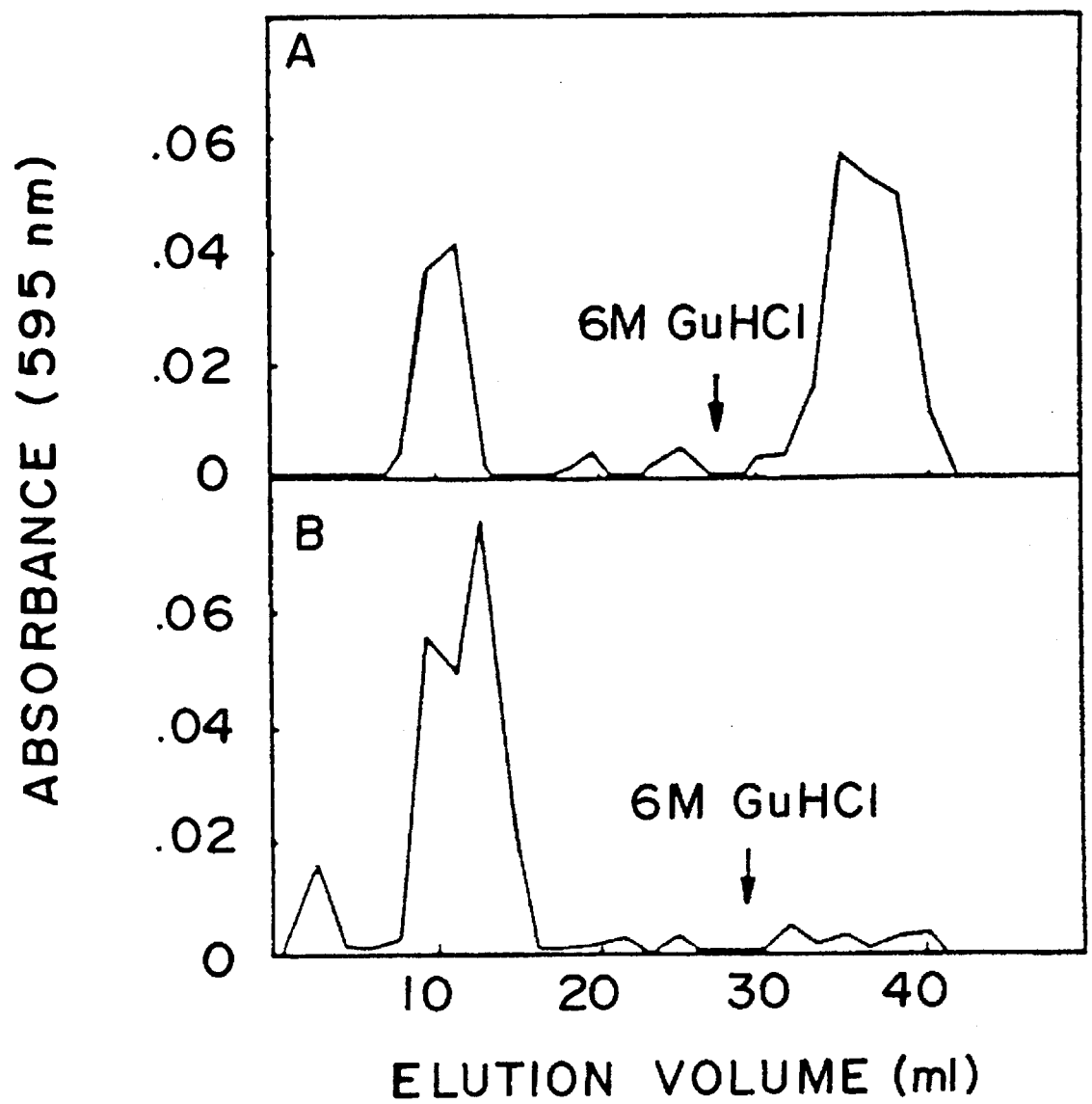
Figure 6:
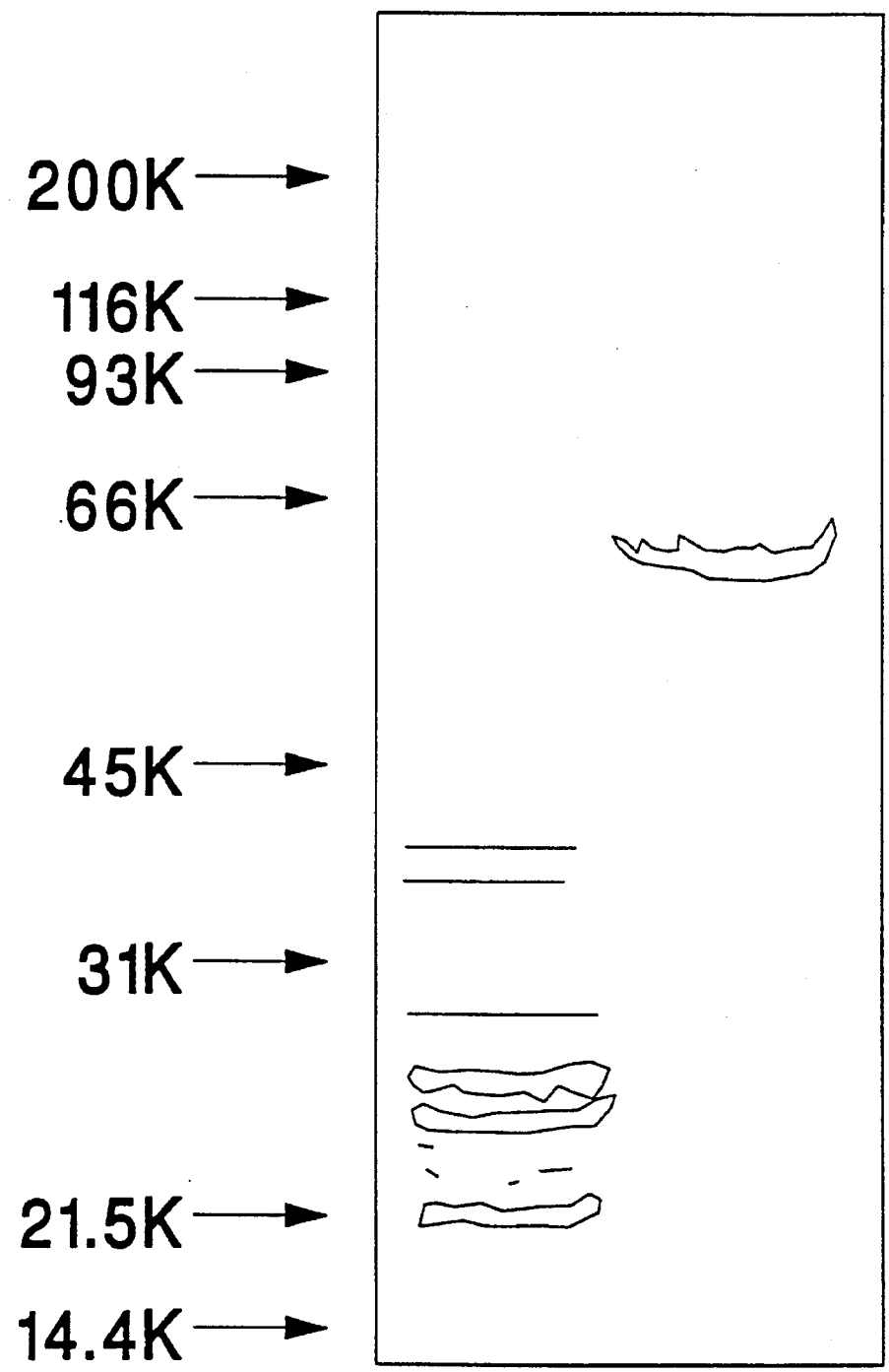

The ZZ-FR protein was bound to the 29 kD $NH_2$-terminal domain of fibronectin and completely inhibited the binding of intact fibronectin to S. aureus (FIGS. 5 and 6). These data indicate that under the incubation conditions used other proteins, recognizing domains outside the 29 kD N-terminus of fibronectin, are not expressed by the staphylococcal cells. Furthermore the fibronectin binding activity of the FNBP has been localized to a fairly small segment of the protein. Recent analysis of the native 210 kD FNBP isolated from S. aureus strain Newman demonstrated that this protein is multivalent and one molecule of the FNBP is capable of binding 6–9 fibronectin molecules (12). The cloned fnbp-gene is derived from strain S. aureus 8325-4. If there are no differences between strains of S. aureus one would except the FR-region to contain several repeating sequences. This question was also answered by sequence analysis of the cloned fnbp-gene. The sequence of the FR-region having FNBP-properties is given in FIG. 8

Figure 9:
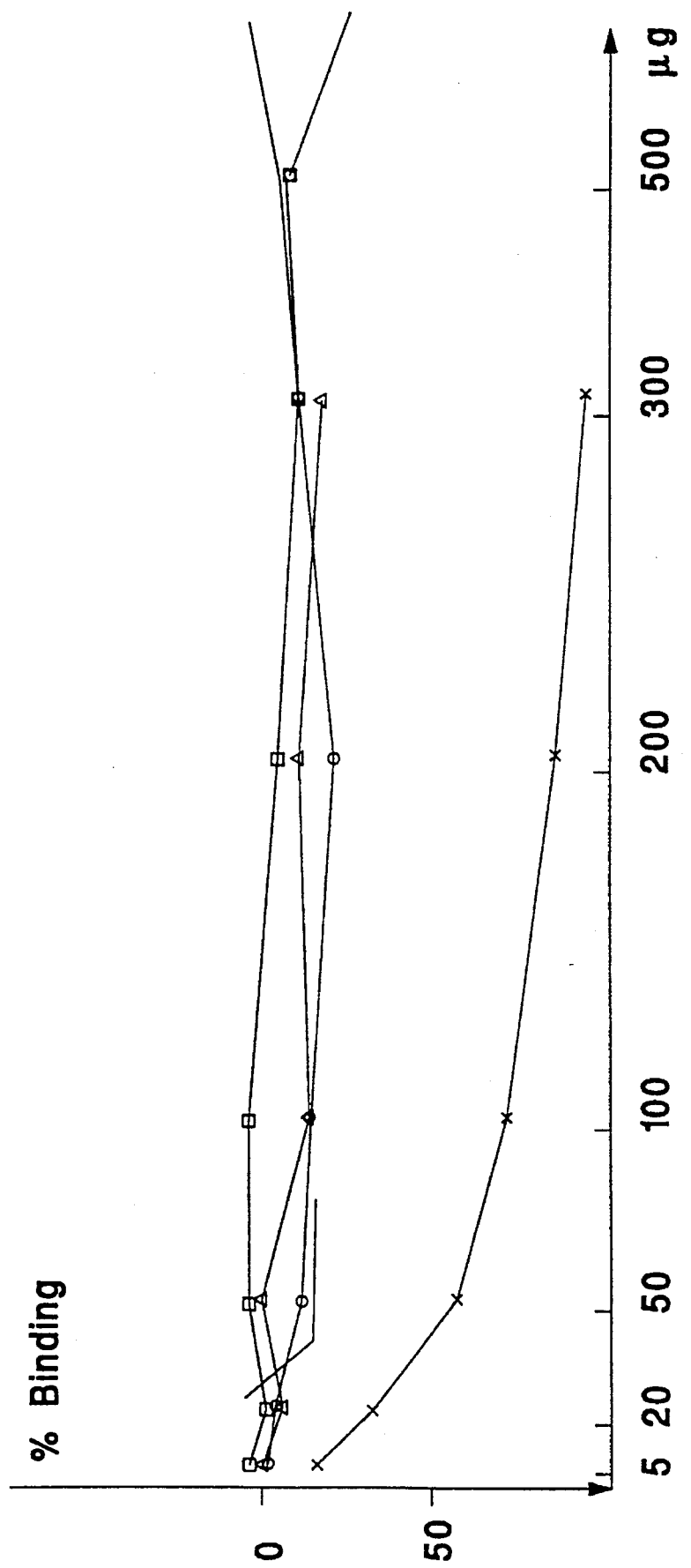

There is reason to believe that the FR binding activity is related to the each of the three 38 amino acids repeats as the Bal1-PvuII-fragment encodes for a binding activity (cf. FIG. 3); as the Bal1-HincII-fragment encodes for a binding activity; and as the HincII-PvuII-fragment does not encode for binding activity. Furthermore, the one single 38 amino acids repeat is functional in binding fibronectin, since a synthezised 38-amino acids long peptide (38(2)-repeat) has binding ability, as shown in FIG. 9. Each of the three 38 amino acids repeats are very homologous

EXAMPLE 2

Chemical synthesis of a polypeptide based on the nucleotide sequence coding for the fibronectin binding domain of 38 amino acids (38(2) repeat) was performed by building up the amino acid sequence corresponding to said nucleotide sequence starting from the C-terminal histidin and stepwise reacting with the appropriate amino acid and finally reacting with the glycine at the N-terminal end, in a solid phase synthesis according to the method by K. B. Merrifield, J. Am. Chem. Soc. 86, pp. 304, (1964). Hereby the polypeptide corresponding to the second 38 amino acid repeat was synthezised, as well as three further polypeptides being parts of this 38-repeat, viz: 1) the poly peptide covering amino acids 1–19, 2) the polypeptide covering amino acids 9–30, and 3) the polypeptide covering amino acids 20–38, were all synthezised according to the same method.

The fibronectin binding ability of the complete 38-repeat, as well as of the 1–19 amino acid polypeptide, the 9–30 amino acid polypeptide, the 20–38 amino acid polypeptide, as well as a mixture of these three smaller polypeptides was tested, and the result is given in FIG. 9. The fragments of the complete 38-repeat were synthezised in order to check if fibronectin binding is dependent upon the complete 38-repeat, as anticipated, or if fibronectin binding properties could be further confined to some smaller regoin of the 38 amino acid sequence. As evident from FIG. 9 the fibronectin binding property is only present in the complete 38 amino acids peptide.

Materials and Methods

Bacterial Strains and Plasmids.

A gene bank in pBR322 of chromosomal DNA from Staphylococcus aureus strain 8325-4, earlier described (13) was screened for clones expressing fibronectin binding activity. E. coli strains HB102, (18) and JM105 (19), were used in subcloning and expression experiments. The plasmid vectors used were pBR322 (20) pUC18 (21) and the protein A vectors pRIT3 (15) and pEZZ318 (16). S. aureus strains Cowan I, Newman and 8325-4 were used in the assay of the fibronectin binding protein (FNBP).

Microorganism Growth Medium

At the culture of E. coli bacteria the following medium was used. The amounts given relates to 1 liter of medium.

| | |
|---|---|
| Trypton Soy Broth (Oxoid Ltd, Basingstoke, Hants, GB) | 30 g |
| Yeast Extract (Oxoid) | 10 9 |
| D-glucose | 40 9 |
| $NH_4Cl$ | 2,5 g |
| $Na_2HPO_4.2H_2O$ | 7,5 g |
| $KH_2PO_4$ | 3,0 g |
| $Na_2SO_4.10H_2O$ | 2,5 g |
| $MgSO_4.7H_2O$ | 0,2 g |
| $CaCl_2.2H_2O$ | 0,5 mg |
| $FeCl_3.6H_2O$ | 16,7 mg |
| $ZnSO_4.7H_2O$ | 0,18 mg |
| $CuSO_4.5H_2O$ | 0,16 mg |
| $MnSO_4.4H_2O$ | 0,15 mg |
| $CoCl_2$ | 0,10 mg |
| NaEDTA | 20,1 mg |

Assay of Fibronectin Binding Protein (FNBP)

Quantitation of fibronectin binding to cells of S. aureus has been described earlier (10). If not otherwise stated, $10^9$ cells of S. aureus Cowan I are incubated with $^{125}$I-labelled fibronectin or the 29 kD $NH_2$-terminal fragment of fibronectin in PBS containing 1 mg/ml bovine serum albumin in a total volume of 0,3 ml. After incubation for 2 hours at 22° C. the radioactivity bound to the cells is measured in a gamma counter.

Lysates of E. coli clones prepared in Tris-HCl buffer, pH 8,1, containing lysozyme EDTA as earlier described (13), were analysed for fibronectin binding activity by measuring their ability to compete with staphylococcal cells for binding the $^{125}$I-labelled 29 kD $NH_2$-terminal fragment of fibronectin. The amount of FNBP able to inhibit binding to 50% is considered as one unit of activity.

An osmotic shock procedure was used to release proteins from the periplasmic space of E. coli (14).

Purification of FNBP

The purification is based on affinity chromatography on fibronectin-Sepharose followed by ion-exchange chromatography.

Human fibronectin was prepared from outdated blood by the method known (22). The fibronectin was then dialysed against 20 mM Tris-HCl, pH 8,3 and concentrated on a DEAE-column. The coupling of fibronectin to Sepharose SL-4B was done by a bromocyan activation procedure as known (23).

The *E. coli* lysate was pumped onto the affinity column which was subsequently washed with 0,5M ammonium acetate until the baseline was stable (about four column volumes). The FNBP was then eluted with 0,4M acetic acid and either neutralized with ammonia or lyophilized. After dialysis against 10 mM ammonium acetate with pH adjusted to 7,6 with ammonia a further fractionation step was performed by ion-exchange chromatography on a Pharmacia FPLC equipment using a mono Q column.

Nucleotide Sequence Analysis

The nucleotide sequence was determined in accordance with the methods described by Maxam, A.M. et al (27).

Amino Acid Analysis

The amino acid composition was determined using a Durrum D-500 analyzer. Samples were hydrolyzed in 6M HCl containing 2 mg/ml phenol for 24 hours at 110° C. One sample was also oxidized with performic acid in oder to determine cystein and methionine. Norluecin was added as an internal standard. Protein was determined according to (24) using bovine serum albumin as a standard.

Electrophoresis

If not indicated otherwise SDS-polyacrylamide gel electroporesis was performed in 5–15% gradient gels. The gels were stained with Coomassie brilliant blue, de-stained and photographed.

Radioimmunoassay Procedure

The purified FNBP with an estimated molecular weight in SDS-polyacrylamide gel electrophoresis of 165 kD was labelled with $^{125}$I-odine by the chloramine-T method as known (25). After the iodination the material was rechromatographed on a fibronectin-Sepharose column.

The incubation mixture contained $^{125}$I-FNBP (3 400 cpm in 10/µl) was mixed with various dilutions of a rabbit antiserum (containing antibodies directed against *S. aureus* strain Newman), in incubation buffer (PBS, 0,1% Triton X-100 and 0,02% sodium azid) in a volume of 0,2 ml.

Samples were for 2 hours at 20° C. to allow antigen-antibody reaction. 0,1 ml of 10% suspension (w/v) of protein A-Sepharose in PBS was added and the mixture was incubated for another hour. The incubation was stopped by adding another 1,7 ml of incubation buffer to the samples. After centrifugation at 2000 rpm for 3 min the supernatants were sucked off. The pellets were washed twice in incubation buffer and the radioactivity associated with the protein A-Sepharose was measured in a gammacounter.

Restriction Endonucleases and Other Enzymes

Restriction enzymes, T4 DNA ligase and Bal31 were purchased from BRL and used according to their recommendations. Other methods involving DNA techniques were essentially as known (26).

TABLE 1

Comparison of amino acid compositions of fibronectin binding proteins (87 and 165 kD) isolated from *E. coli* pFR001 and the native FNBP isolated from *S. aureus* strain Newman (210 kD).

| Amino acid | Composition (mol %) | | |
|---|---|---|---|
| | 210 kD[a] | 165 kD | 87 kD |
| Aspartic acid/asparagine | 15.4 | 14.6 | 13.4 |
| Threonine | 9.7 | 10.7 | 10.3 |
| Serine | 7.4 | 6.5 | 8.0 |
| Glutamic acid/glutamine | 17.9 | 17.1 | 15.1 |
| Proline | 6.3 | 6.2 | 5.8 |
| Glycine | 8.9 | 7.9 | 8.4 |
| Alanine | 5.3 | 4.6 | 4.7 |
| Half-cystine | 0.1 | 0.2 | n.d. |
| Valine | 7.2 | 7.8 | 8.6 |
| Methionine | 0.6 | 0.6 | n.d. |
| Isoleucine | 4.3 | 4.7 | 3.8 |
| Leucine | 4.1 | 4.0 | 4.6 |
| Tyrosine | 2.1 | 2.3 | 4.1 |
| Phenylalanine | 2.4 | 2.0 | 3.6 |
| Histidine | 1.0 | 3.2 | 3.0 |
| Lysine | 5.3 | 6.3 | 6.6 |
| Tryptophan | n.d. | n.d. | n.d. |
| Arginine | 1.9 | 1.2 | — |

[a] from Fröman et al. (1987), (12).
n.d. = not determined

The present fibronectin binding protein can be used for immunization, whereby the protein, preferably in combination with a fusion protein to create a large antigen to respond to, is injected in dosages causing immunological reaction in the host mammal. Thus the fibronectin binding protein can be used in vaccination of ruminants against mastitis caused by Staphylococcal infections. The fibronectin binding protein of this invention has shown to form antibodies against a staphylococcal mastitis in a mouse model as shown in the Table below.

TABLE

Experimental mouse mastitis produced by *S. aureus* strain SA 113(83A) in a dose of $1,0 \times 10^3$ cfu. Evaluation of immunization using 15/µg protein per mouse of the fibronectin binding protein expressed from *E. coli* containing plasmid pFR001 as identified herein.

TABLE

Experimental mouse mastitis produced by *S. aureus* strain SA 113(83A) in a dose of $1,0 \times 10^3$ cfu. Evaluation of immunization using 15/ug protein per mouse of the fibronectin binding protein expressed from *E. coli* containing plasmid pFR001 as identified herein.

| Group of mice | No. of mammary glands inocul. | Gross examination type of lesion (%) | | | | No. of mammary glands invest. | Microscopic type of lesion (%) | | | | |
|---|---|---|---|---|---|---|---|---|---|---|---|
| | | +++ | ++ | + | 0 | | A | B | C1 | C2 | C3 |
| Vaccinated (FNBP) | 30 | 3 | 8 | 83 | 10 | 11 | 9 | 0 | 0 | 91 | 0 |
| Control | 38 | 50 | 16 | 32 | 3 | 8 | 38 | 0 | 25 | 38 | 0 |

TABLE-continued

Experimental mouse mastitis produced by *S. aureus* strain SA 113(83A) in a dose of 1,0 × 10³ cfu. Evaluation of immunization using 15/ug protein per mouse of the fibronectin binding protein expressed from *E. coli* containing plasmid pFR001 as identified herein.

| Group of mice | No. of mammary glands inocul. | Gross examination type of lesion (%) | | | | No. of mammary glands invest. | Microscopic type of lesion (%) | | | | |
|---|---|---|---|---|---|---|---|---|---|---|---|
| | | +++ | ++ | + | 0 | | A | B | C1 | C2 | C3 |

Mastitis: +++ = gross; ++ = medium-grade; + = Low grade; 0 = no macroscopic changes; A = consistently non-reactive, total necrosis; B = advanced regressive changes + slight inflammatory reaction; C1 = disseminated inflammatory reaction + local necrosis; C2 = disseminated inflammatory reaction; C3 = local inflammatory reaction; 0 = no reaction.

As evident from the Table above a consistent immunization is obtained using the FNBP as expressed by the *E. coli* containing the plasmid pFR001.

Further, the fibronectin binding protein can be used to block an infection in an open skin wound by wound treatment using the fibronectin binding protein in a suspension. Thus the fibronectin binding protein can be used for the treatment of wounds, e.g. for blocking protein receptors, or for immunization (vaccination). In the latter case the host body produces specific antibodies, which can protect against invasion of bacterial strains comprising such a fibronectin binding protein. Hereby the antibodies block the adherence of the bacterial strains to damaged tissue.

Examples of colonization and tissue damage are:
a) colonizing of wounds in skin and connective tissue, which wounds have been caused by a mechanical trauma, chemical damage, and/or thermical damage;
b) colonizing of wounds on mucous membranes, such as in the mouth cavity, or in the mammary glands, urethra, or vagina;
c) colonizing on connective tissue proteins, which have been exposed by a minimal tissue damage (microlesion) in connection with epithelium and endothelium (mastitis, heart valve infection, hip exchange surgery).

When using the present FNBP, or the 38 amino acid polypeptide, for the purpose of immunization (vaccination) in mammals, including man, the protein, or polypeptide is dispersed in sterile, isotonic saline solution, optionally while adding a pharmaceutically acceptable dispersing agent. Different types of adjuvants can further be used in order to sustain the release in the tissue, and thus expose the protein or the peptide for a longer time to the immundefense system of a body.

A suitable dosage to obtain immunization is 0,5 to 5/µg of FNBP, or polypeptide, per kg bodyweight and injection of immunization. In order to obtain a durable immunization, vaccination should be carried out at more than one consecutive occasions with an interval of 1 to 3 weeks, preferably at three occasions.

When using the present FNBP, or polypeptide, for topical, local administration the protein is dispersed in an isotonic saline solution to a concentration of 25 to 250/µg per ml. The wounds are then treated with such an amount only to obtain a complete wetting of the wound surface. For an average wound thus only a couple of milliliters of solution are used in this way. After treatment using the protein solution the wounds are suitably washed with isotonic saline or another suitable wound treatment solution.

Further the fibronectin binding protein as well as the minimal fibronectin binding site polypeptide., of the present invention can be used to diagnose bacterial infections caused by Staphylococci strains, whereby a fibronectin binding protein of the present invention is immobilized on a solid carrier, such as small latex or Sepharose[R] beads, whereupon sera containing antibodies are allowed to pass and react with the FNBP thus immobilized. The agglutination is then measured by known methods.

Further, the FNBP, or the polypeptide can be used in an ELISA test (Enzyme Linked Immuno Sorbent Assay; E Engvall, Med. Biol. 55, 193, (1977)). Hereby wells in a polystyrene microtitre plate are coated with the FNBP, and incubated over night at 4° C. The plates are then thoroughly washed using PBS containing 0.05% TWEEN 20, and dried. Serial dilution of the patient serum were made in PBS-Tween, were added to the wells, and incubated at 30° C. for 1.5 hrs. After rinsing antihuman-IgG conjugated with an enzyme, or an antibovine-IgG conjugated with an enzyme, respectivel, horseradishperoxidase or an alkaline phosphatase, was added to the wells and incubated at 30° C. for 1,5 hrs, whereupon when the IgG has been bound thereto, and after rinsing, an enzyme substrate is added, a p-nitrophosphate in case of an alkaline phosphatase, or ortophenylene diamine substrate (OPD) in case a peroxidase has been used, respectively. The plates comprising the wells were thus then rinsed using a citrate buffer containing 0.055% OPD, and 0.005% $H_2O_2$, and incubated at 30° C. for 10 min. Enzyme reaction was stopped by adding a 4N solution of $H_2SO_4$ to each well. The colour development was measured using a spectrophotometer.

Depending on the type of enzyme substrate used a fluoroscense measurement can be used as well.

Another method to diagnose Staphylococci infections is by using the DNA gene probe method based on the FNBP sequence or the 38 amino acid polypeptide sequence. Thereby the natural or synthetic DNA sequences are attached to a solid carrier, such as a polystyrene plate as mentioned above, by e.g. adding a milk in the case of diagnozing a mastitis, to the surface. The DNA gene probe, optionally labelled enzymatically, or by a radioactive isotope is then added to the solid surface plate comprising the DNA sequence, whereby the DNA gene probe attaches to the sequence where appearing. The enzyme or the radioactive isotope can then readily be determined by known methods.

Above the term fibronectin binding protein includes any of the 38 amino acid polypeptide sequences as well, which 38 amino acid polypeptide sequences forms the minimal fibronectin binding site of the complete protein.

REFERENCES

8. Beachey, E. H. and Simpson, W. A (1982). Infection 10, 107–110.

20. Bolivar, F., Rodriquez, R. L., Greene, P. J., Betlach, M. C., Heyneker, H:L., Boyer, H. W., Crosa, J. H. and Falkow, S. (1977). Gene, 2, 95–113.
18. Boyer, H. W. and Roulland-Dussoix, D. (1969). J. Mol.Biol: 41, 459–472.
9. Courtney, H. S., Ofek,I., Simpson, W. A., Hasty, D. L. and Beachey, E. H. (1986). Infect. Immun. 53, 454–459.
11. Espersen, F. and Clemmensen, I. (1982). Infect. Immun. 37, 526–531.
17. Fröman, G., Switalski, L. M., Guss, B., Lindberg., M., Höök, M. and Wadström, T. (1986) In Lark, D. L. ed. Protein-Carbohydrate Interactions in Biological Systems. Academic Press, London, pp. 263–268.
12. Fröman, G., Switalski, L. M., Speziale, P. and Hook, M. (1987) in press. J. Biol. Chem.
25. Hunter, W. M. (1978) Radioimmunoassay. In: Wier, K. M. ed. Handbook of Experimental Immunology. London Blackwell. 14.1–14.40.
1. Hynes, R. O. (1985) Annu. Rev. Cell Biol. 1 , 67–90.
2. Hynes, R. O. (1986) Sci. Ann. 254, 42–51.
6. Kuusela, P. (1978) Nature 276, 718–720.
24. Lowry, O. H., Rosebrough, N. J., Farr, A. L. and Randall, R. J., Biol. Chem. 193, 265–275.
13. Löfdahl, S., Guss B., Uhleén, M., Philipson, L. and lindberg, M. (1983) Proc. Natl. Acad. Sci. USA 80, 697–701.
26. Maniatis, T., Fritsch, E. F. and Sambrok, J. (1982). Molecular cloning: a laboratory manual, Cold Spring Harbor Laboratory, New York.
23. March, S. C., Parikh, I. and Cuatrecasas, P. (1974) . Analyt. Biochem. 60, 149–152.
27, Maxam, A. M. and Gilbert, W., (1977), Proc. Natl. Acad. Sci., USA, 74, 560.
28. Merrifield, K. B., J. Am. Chem. Soc., 86, pp. 304, (1964)
19. Messing, J. and Carlsson, J. (1984). J. Biotechnol. 1, 253–264.
22. Miekka, S. I., Ingham, K. C. and Menache, D. (1982). Thromb Res. 27, 1–14.
15. Nilsson, B., Abrahamsún, 1. and Uhlén, M. (1985). EMBO J. 4, 1075–1080.
16. Nilsson, B., Moks, T., Jansson, B., Abrahamsén, Elmblad, A., Holmgren, E., Henrichson, L., Jones, T. A. and Uhlén, M. (1986). Protein Engineering, In press.
21. Norrander, J., Kempe, T. and Messing, J. (1983). Gene, 26, 101–106.
14. Nossal, N. G. and Heppel, L. A. (1965). J . Biol. Chem. 241, 3055–3062.
3. Ruoslahti, E. and Pierschbacher, M. D. (1986). Cell, 44, 517–518.
10. Rydén, C., Rubin, K., Speziale, P., Höök, M., Lindberg, M. and Wadström, T. (1983), J. Biol. Chem. 258, 3396–3401.
7. Wadström, T., Switalski, L., Speziale, P., Rubin, K., Ryd én, C., Fröman, G., Faris, A., Lindberg, M., Höök, M., (1985), In Jackson, G. J. (ed), Pathogenesis of Infection. Springer Verlag, Berlin, Heidelberg, New York, Tokyo, pp. 193–207.
4. Woods, A., Couchman, J. R., Johansson, S., and Höök, M. (1986), EMBO J. 5, 665–670.
5. Yamada, K. M. (1983), Annu. Rev. Biochem. 52, 761–799.

LEGENDS TO THE FIGURES

FIG. 1A. Affinity Chromatography on Fibronectin-Sepharose

A lysate (86 ml) obtained by cold osmotic shock of the *E. coli* clone pFR001 was mixed with 29 ml of 2M ammonium acetate. The sample was then applied to a column (1.9×5.7 cm) equilibrated with 0.5M ammonium acetate at a flow rate of 50 ml/h. After the application of the sample the column was washed with four column volumes of 0.5M ammonium acetate at a flow rate of 20 ml/h. At the same time the sensitivity of the UV-monitor was increased by a factor of five. The material eluting between 200 and 220 ml was pooled, neutralized with ammonium hydroxide and dialysed against 10 mM ammonium acetate, pH 7.6.

FIG. 1B. Ion-Exchange Chromatography

A sample (10 ml) of the dialysed material from the affinity-chromatography described in FIG. 1A was applied to a 1 ml Mono Q (Pharmacia, Sweden) anion column equilibrated with 10 mM ammonium acetate, pH 7.6. The flow rate was 2 ml/min and the column was eluted by a liner increase in the concentration of ammonium acetate of 25 mM per ml. The two peaks (I and II) were pooled as indicated in the figure.

FIG. 2. Polyacrylamide Gel Electrophoresis of Materials From the Different Purification Steps of an Osmotic Shock Lysate of *E. coli* pfr001

Material applied (lane 1) to the affinity column (fibronectin-Sepharose), unadsorbed (lane 2) and adsorbed (lane 3) material. Ion exchange chromatography of affinity purified material on a Mono Q FPLC column (Pharmacia, Sweden): pool I (lane 4) and pool II (lane 5) as marked in FIG. 1B.

Figure 3:
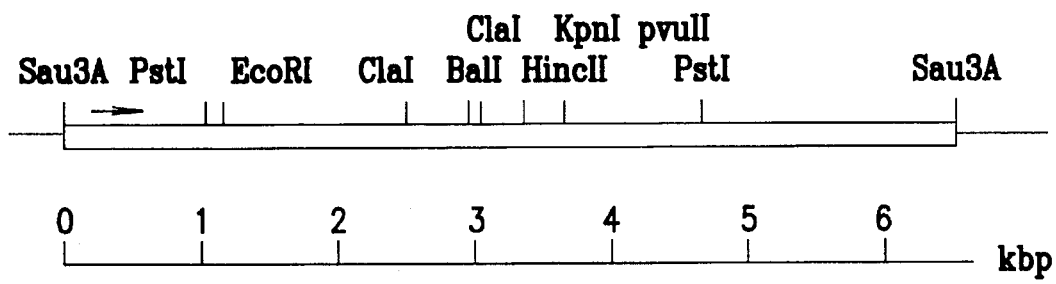

FIG. 3. Restriction Map, Subclones and Deletions of the Insert in pfr001
(A) Restriction map of the 6.5 kb insert. (B) various subclones constructed in order to determine the region of the gene which codes for the fibronectin binding activity. (C) Deletions made from either the 3' or the 5' end of the EcoRI-PstI-fragment by treatment with exonuclease Bal31 (see text for details). The fibronectin binding activity for the differnt gene products is indicated.

FIG. 4. Polyacrylamide Gel Electrophoresis of the Zz-Fr Protein

Protein A (Sigma Chemical Co, St. Louis; lane A) arid the ZZ-FR fusion protein (lane B) were reduced and subjected to electrophoresis in SDS on a 5–15% polyacrylamide gel. The gel was subsequently stained with Coomassie blue. In lanes C & D the ZZ-FR fusion protein and protein A, respectively, were fractionated by SDS-electrophoresis on a 5–9% polyacrylamide gel, electroblotted to nitrocellulose paper and probed with $^{125}$I-labelled 29 kD fibronectin fragment as described (Fröman et al, 1987). Arrows indicate the migration distance of standard proteins of known molecular weights.

FIG. 5. Affinity Chromatography of the Zz-Fr Protein

The ZZ-FR fusion protein (0.6 panel A) and protein A (Sigma; ma Chemical Co; 0,5 mg; panel B) were applied to a 7 ml column of Sepharose 4B CL substituted with 29 kD fibronectin fragment. The column was washed with 0.5M NaCl in PBS and subsequently eluted with 6M GuHCl in PBS. Fractions of 2 ml were collected and assayed for protein using the BioRad system.

FIG. 6. Polyacrylamide Gel Electrophoresis of the Zz-Fr Fusion Protein Preparation, Fractionated by Affinity Chromatography Material not bound (lane A) and bound and eluted (lane B), respectively, from the 29 kD affinity column was analyzed by SDS-gel electrophoresis on 5–15% polyacrylamide gels. The gel was subsequently stained with Coomassie blue. Arrows indicate the migration distance of standard proteins of known molecular weights.

FIG. 7. Inhibition of Binding $^{125}$I-Fibronectin to Bacterial Cells.

Staphylococcal cells ($5 \times 10^7$) of strain Newman (panel A) or strain 8325-4 (panel B) were incubated with $5 \times 10^4$ cpm of $^{125}$I-labelled intact fibronectin (o—o) or 29 kD N-terminal fibronectin fragment (Δ—Δ) in PBS supplemented with 0,1% BSA, and 0.1% Tween$^R$ 80 in a total volume of 0.5 ml for 1 hr in the presence of increasing amounts of ZZ-FR fusion protein or protein A (●—●). For further details of the binding assay used, see Fröman et al (1987). The amounts of $^{125}$I-radioactivity associated with bacterial cells was quantitated and the extent of fibronectin binding calculated. One hundred percent binding represent $^{125}$I-ligand bound to bacteria in absence of inhibiting protein and 0% binding corresponded to radioactivity recorded from incubation mixtures without bacteria.

Figure 8A.1:
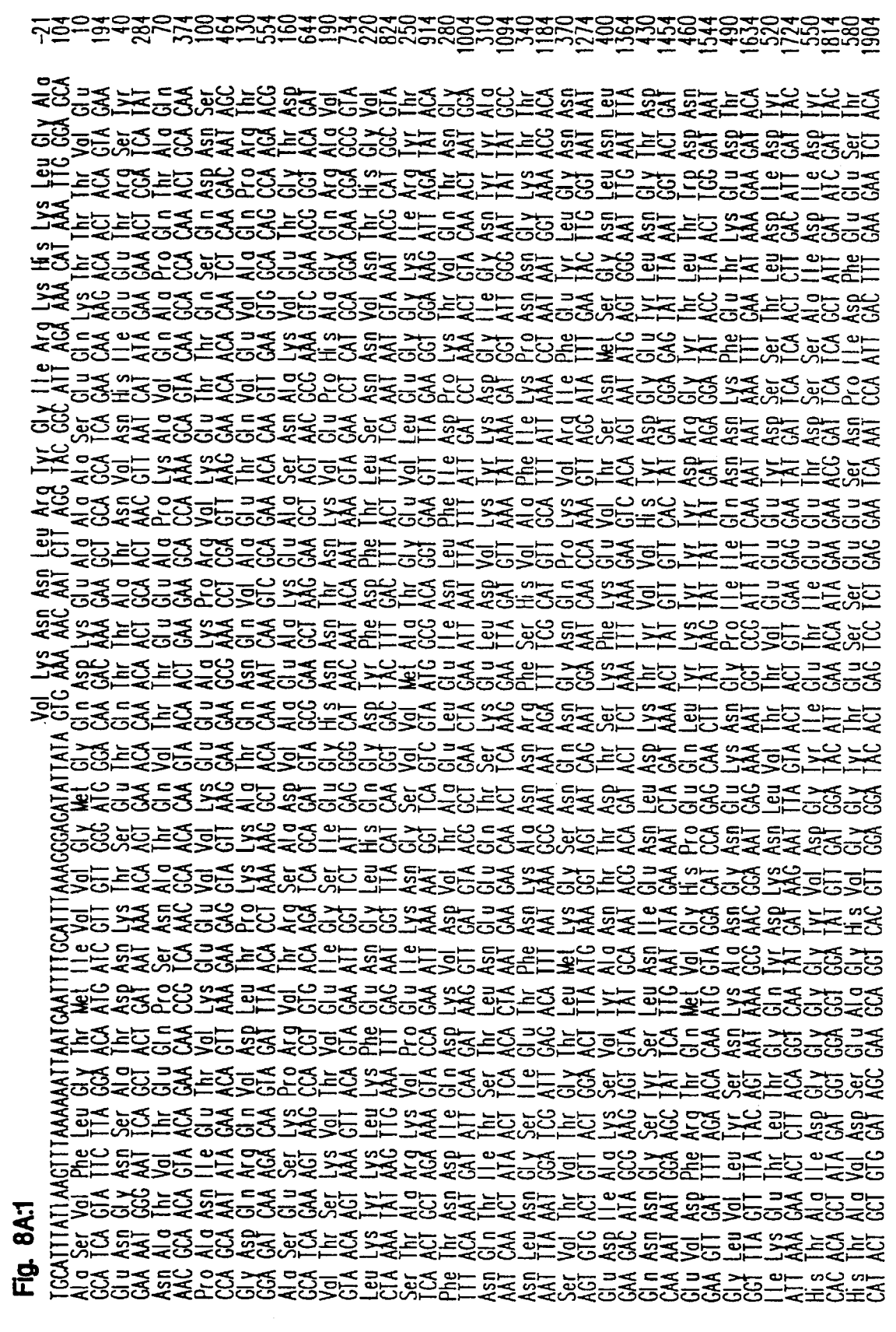
Figure 8A:
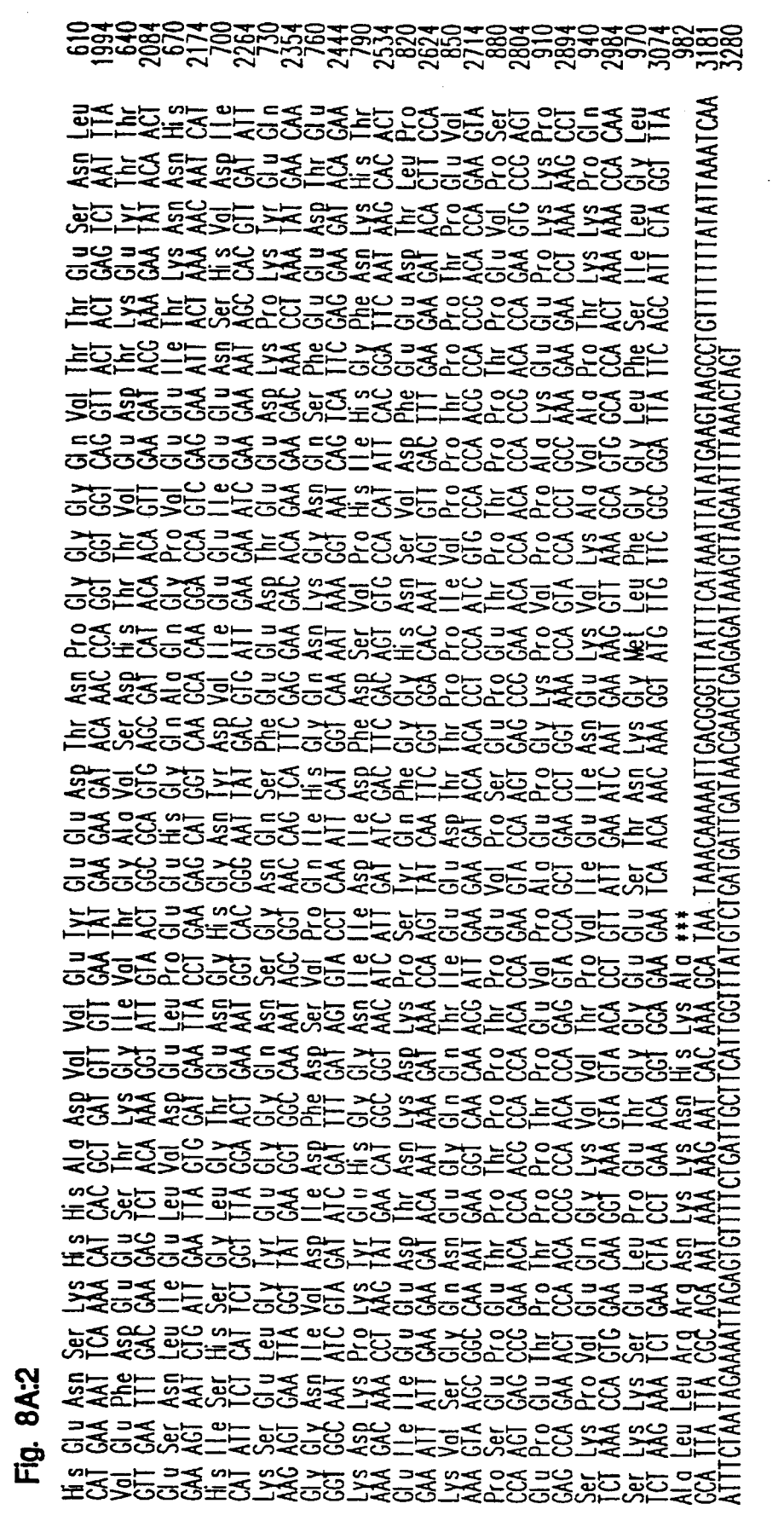

FIG. 8A. [SEQ ID NO. 4] Sequence of Nucleotide Coding For Fibronectin Binding Protein The nucleotide sequence coding for the fibronectin binding protein together with its corresponding amino acids is given. The different 38-amino acids repeats are marked, as well as appearing following almost four complete 14 amino acids repeats. The restriction sites BalI-HincII-PvuII have been noted in the figure, as well as have the amino acids sequences corresponding to the different nucleotide sequences.

FIG. 9 The Fibronectin Binding Ability of a Chemically Synthezised Polypeptide

The fibronectin binding ability of the chemically synthezised 38 amino acids polypeptide according to Example 2 together with the fibronectin binding ability of the fragments of said polypeptide have been tested. (*—*) denotes the polypeptide corresponding to the 38(2) repeat of the amino acids sequence; (□-□) denotes the polypeptide corresponding to amino acids 1–19 of the amino acids sequence; (o—o) denotes the polypeptide corresponding to amino acids 20–38 of the amino acids sequence; (Δ—Δ) denotes the polypeptide corresponding to amino acids no. 9–30 of the amino acids sequence; and (- - -) the polypeptide mixture comprising the polypeptidis of amino acids 1–19, amino acids 20–38, amino acids 9–30. The binding ability in percent has been plotted against μg of polypeptide added.

We claim:

1. A vaccine composition comprising an effective amount of a protein encoded by a hybrid DNA molecule comprising a nucleotide sequence from *Staphylococcus aureus* encoding an isolated protein having fibronectin binding activity, whereby said protein induces immunization by forming antibodies in a mammal against *Staphylococcus aureus* to provide protection for clinical symptoms to *Staphylococcus aureus* wherein the hybrid DNA molecule comprises one or more of the nucleotide sequences selected from the group consisting of nucleotides 1–114 of [SEQ ID NO. 2], nucleotides 115–228 of [SEQ ID NO. 2], and nucleotides 229–342 of [SEQ ID NO. 2]: and a pharmaceutical acceptable vaccine carrier therefor.

2. A vaccine composition comprising an effective amount of a protein encoded by a hybrid DNA molecule comprising a nucleotide sequence from *Staphylococcus aureus* encoding an isolated protein having fibronectin binding activity, whereby said protein induces immunization by forming antibodies in a mammal against *Staphylococcus aureus* to provide protection for clinical symptoms to *Staphylococcus aureus*, wherein the hybrid DNA molecule comprises the nucleotide sequence set forth in [SEQ ID NO. 4] and a pharmaceutically acceptable vaccine carrier therefor.

3. The vaccine composition of claim 2, wherein said mammal is a ruminant.

4. The vaccine composition of claim 2, wherein said mammal is a bovine.

5. The vaccine composition of claim 2, wherein said mammal is a human.

6. A vaccine composition comprising an effective amount of a protein encoded by a plasmid or phage comprising a nucleotide sequence from *Staphylococcus aureus* encoding an isolated protein having fibronectin binding activity, whereby said sequence of the plasmid or phage comprises [SEQ ID NO. 4] and a pharmaceutically acceptable vaccine carrier therefor.

7. A vaccine composition comprising an effective amount of a protein, whereby said protein induces immunization by forming antibodies against *Staphylococcus aureus* to provide protection for clinical symptoms to *Staphylococcus aureus*, wherein the protein comprises the amino acid sequence of [SEQ ID NO. 3] and a pharmaceutically acceptable vaccine carrier therefor.

8. A vaccine composition comprising an effective amount of a protein encoded by plasmid pFR001 as contained in *Escherichia coli* strain 259 having the deposit number DSM 4124, said plasmid comprising a nucleotide sequence from *Staphylococcus aureus* encoding an isolated protein having fibronectin binding activity, whereby said protein induces immunization in a mammal by forming antibodies against *Staphylococcus aureus*, and a pharmaceutically acceptable vaccine carrier therefor.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 558 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
GGCCAAAATA  GCGGTAACCA  GTCATTCGAG  GAAGACACAG  AAGAAGACAA  ACCTAAATAT      60
GAACAAGGTG  GCAATATCGT  AGATATCGAT  TTTGATAGTG  TACCTCAAAT  TCATGGTCAA     120
AATAAAGGTA  ATCAGTCATT  CGAGGAAGAT  ACAGAAAAAG  ACAAACCTAA  GTATGAACAT     180
GGCGGTAACA  TCATTGATAT  CGACTTCGAC  AGTGTGCCAC  ATATTCACGG  ATTCAATAAG     240
CACACTGAAA  TTATTGAAGA  AGATACAAAT  AAAGATAAAC  CAAGTTATCA  ATTCGGTGGA     300
CACAATAGTG  TTGACTTTGA  AGAAGATACA  CTTCCAAAAG  TAAGCGGCCA  AAATGAAGGT     360
CAACAAAGCA  TTGAAGAAGA  TACAACACCT  CCAATCGTGC  CACCAACGCC  ACCGACACCA     420
GAAGTACCAA  GTGAGCCGGA  AACACCAACG  CCACCAACAC  CAGAAGTACC  AAGTGAGCCG     480
GAAACACCAA  CACCACCGAC  ACCAGAAGTG  CCGAGTGAGC  CAGAAACTCC  AACACCGCCA     540
ACACCAGAGG  TACCAGCT                                                     558
```

( 2 ) INFORMATION FOR SEQ ID NO:2:

( i ) SEQUENCE CHARACTERISTICS:
        ( A ) LENGTH: 342 base pairs
        ( B ) TYPE: nucleic acid
        ( C ) STRANDEDNESS: single
        ( D ) TOPOLOGY: linear (i i) MOLECULE TYPE: DNA (genomic)

(x i) SEQUENCE DESCRIPTION: SEQ ID NO:2:

| | | | | | |
|---|---|---|---|---|---|
| GGCCAAAATA | GCGGTAACCA | GTCATTCGAG | GAAGACACAG | AAGAAGACAA | ACCTAAATAT | 60 |
| GAACAAGGTG | GCAATATCGT | AGATATCGAT | TTTGATAGTG | TACCTCAAAT | TCATGGTCAA | 120 |
| AATAAAGGTA | ATCAGTCATT | CGAGGAAGAT | ACAGAAAAAG | ACAAACCTAA | GTATGAACAT | 180 |
| GGCGGTAACA | TCATTGATAT | CGACTTCGAC | AGTGTGCCAC | ATATTCACGG | ATTCAATAAG | 240 |
| CACACTGAAA | TTATTGAAGA | AGATACAAAT | AAAGATAAAC | CAAGTTATCA | ATTCGGTGGA | 300 |
| CACAATAGTG | TTGACTTTGA | AGAAGATACA | CTTCCAAAAG | TA | | 342 |

(2) INFORMATION FOR SEQ ID NO:3:

(i) SEQUENCE CHARACTERISTICS:
(A) LENGTH: 114 amino acids
(B) TYPE: amino acid
(C) STRANDEDNESS: single
(D) TOPOLOGY: linear (i i) MOLECULE TYPE: protein (x i) SEQUENCE DESCRIPTION: SEQ ID NO:3:

Gly Gln Asn Ser Gly Asn Gln Ser Phe Glu Glu Asp Thr Glu Glu Asp
1               5                   10                  15

Lys Pro Lys Tyr Glu Gln Gly Gly Asn Ile Val Asp Ile Asp Phe Asp
            20                  25                  30

Ser Val Pro Gln Ile His Gly Gln Asn Lys Gly Asn Gln Ser Phe Glu
                35                  40                  45

Glu Asp Thr Glu Lys Asp Lys Pro Lys Tyr Glu His Gly Gly Asn Ile
            50                  55                  60

Ile Asp Ile Asp Phe Asp Ser Val Pro His Ile His Gly Phe Asn Lys
65                  70                  75                  80

His Thr Glu Ile Ile Glu Glu Asp Thr Asn Lys Asp Lys Pro Ser Tyr
                    85                  90                  95

Gln Phe Gly Gly His Asn Ser Val Asp Phe Glu Glu Asp Thr Leu Pro
                100                 105                 110

Lys Val (2) INFORMATION FOR SEQ ID NO:4:

(i) SEQUENCE CHARACTERISTICS:
(A) LENGTH: 3280 base pairs
(B) TYPE: nucleic acid
(C) STRANDEDNESS: single
(D) TOPOLOGY: linear (i i) MOLECULE TYPE: DNA (genomic)

(i x) FEATURE:
(A) NAME/KEY: CDS
(B) LOCATION: 57..3114

(x i) SEQUENCE DESCRIPTION: SEQ ID NO:4:

TGCATTTATT AAGTTTAAAA AATTAATGAA TTTTGCATTT AAAGGGAGAT ATTATA    56

GTG AAA AAC AAT CTT AGG TAC GGC ATT AGA AAA CAT AAA TTG GGA GCA    104
Val Lys Asn Asn Leu Arg Tyr Gly Ile Arg Lys His Lys Leu Gly Ala
1               5                   10                  15

GCA TCA GTA TTC TTA GGA ACA ATG ATC GTT GTT GGG ATG GGA CAA GAC    152
Ala Ser Val Phe Leu Gly Thr Met Ile Val Val Gly Met Gly Gln Asp
            20                  25                  30

AAA GAA GCT GCA GCA TCA GAA CAA AAG ACA ACT ACA GTA GAA GAA AAT    200

| | | | | | | | | | | | | | | |
|---|---|---|---|---|---|---|---|---|---|---|---|---|---|---|
| Lys | Glu | Ala | Ala | Ala | Ser | Glu | Gln | Lys | Thr | Thr | Thr | Val | Glu | Glu | Asn |
| | | 35 | | | | | 40 | | | | | 45 | | | |

| GGG | AAT | TCA | GCT | ACT | GAT | AAT | AAA | ACA | AGT | GAA | ACA | CAA | ACA | ACT | GCA | 248 |
|---|---|---|---|---|---|---|---|---|---|---|---|---|---|---|---|---|
| Gly | Asn | Ser | Ala | Thr | Asp | Asn | Lys | Thr | Ser | Glu | Thr | Gln | Thr | Thr | Ala | |
| | 50 | | | | | 55 | | | | | 60 | | | | | |

| ACT | AAC | GTT | AAT | CAT | ATA | GAA | GAA | ACT | CGA | TCA | TAT | AAC | GCA | ACA | GTA | 296 |
|---|---|---|---|---|---|---|---|---|---|---|---|---|---|---|---|---|
| Thr | Asn | Val | Asn | His | Ile | Glu | Glu | Thr | Arg | Ser | Tyr | Asn | Ala | Thr | Val | |
| 65 | | | | | 70 | | | | | 75 | | | | | 80 | |

| ACA | GAA | CAA | CCG | TCA | AAC | GCA | ACA | CAA | GTA | ACA | ACT | GAA | GAA | GCA | CCA | 344 |
|---|---|---|---|---|---|---|---|---|---|---|---|---|---|---|---|---|
| Thr | Glu | Gln | Pro | Ser | Asn | Ala | Thr | Gln | Val | Thr | Thr | Glu | Glu | Ala | Pro | |
| | | | | 85 | | | | | 90 | | | | | 95 | | |

| AAA | GCA | GTA | CAA | GCA | CCA | CAA | ACT | GCA | CAA | CCA | GCA | AAT | ATA | GAA | ACA | 392 |
|---|---|---|---|---|---|---|---|---|---|---|---|---|---|---|---|---|
| Lys | Ala | Val | Gln | Ala | Pro | Gln | Thr | Ala | Gln | Pro | Ala | Asn | Ile | Glu | Thr | |
| | | | 100 | | | | | 105 | | | | | 110 | | | |

| GTT | AAA | GAA | GAG | GTA | GTT | AAG | GAA | GAA | GCG | AAA | CCT | CGA | GTT | AAG | GAA | 440 |
|---|---|---|---|---|---|---|---|---|---|---|---|---|---|---|---|---|
| Val | Lys | Glu | Glu | Val | Val | Lys | Glu | Glu | Ala | Lys | Pro | Arg | Val | Lys | Glu | |
| | | | 115 | | | | | 120 | | | | | 125 | | | |

| ACA | ACA | CAA | TCT | CAA | GAC | AAT | AGC | GGA | GAT | CAA | AGA | CAA | GTA | GAT | TTA | 488 |
|---|---|---|---|---|---|---|---|---|---|---|---|---|---|---|---|---|
| Thr | Thr | Gln | Ser | Gln | Asp | Asn | Ser | Gly | Asp | Gln | Arg | Gln | Val | Asp | Leu | |
| | 130 | | | | | 135 | | | | | 140 | | | | | |

| ACA | CCT | AAA | AAG | GCT | ACA | CAA | AAT | CAA | GTC | GCA | GAA | ACA | CAA | GTT | GAA | 536 |
|---|---|---|---|---|---|---|---|---|---|---|---|---|---|---|---|---|
| Thr | Pro | Lys | Lys | Ala | Thr | Gln | Asn | Gln | Val | Ala | Glu | Thr | Gln | Val | Glu | |
| 145 | | | | | 150 | | | | | 155 | | | | | 160 | |

| GTG | GCA | CAG | CCA | AGA | ACG | GCA | TCA | GAA | AGT | AAG | CCA | GCT | GTG | ACA | AGA | 584 |
|---|---|---|---|---|---|---|---|---|---|---|---|---|---|---|---|---|
| Val | Ala | Gln | Pro | Arg | Thr | Ala | Ser | Glu | Ser | Lys | Pro | Ala | Val | Thr | Arg | |
| | | | | 165 | | | | | 170 | | | | | 175 | | |

| TCA | GCA | GAT | GTA | GCG | GAA | GCT | AAG | GAA | GCT | AGT | AAC | GCG | AAA | GTC | GAA | 632 |
|---|---|---|---|---|---|---|---|---|---|---|---|---|---|---|---|---|
| Ser | Ala | Asp | Val | Ala | Glu | Ala | Lys | Glu | Ala | Ser | Asn | Ala | Lys | Val | Glu | |
| | | | 180 | | | | | 185 | | | | | 190 | | | |

| ACG | GGT | ACA | GAT | GTA | ACA | AGT | AAA | GTT | ACA | GTA | GAA | ATT | GGT | TCT | ATT | 680 |
|---|---|---|---|---|---|---|---|---|---|---|---|---|---|---|---|---|
| Thr | Gly | Thr | Asp | Val | Thr | Ser | Lys | Val | Thr | Val | Glu | Ile | Gly | Ser | Ile | |
| | | 195 | | | | | 200 | | | | | 205 | | | | |

| GAG | GGG | CAT | AAC | AAT | ACA | AAT | AAA | GTA | GAA | CCT | CAT | GCA | GGA | CAA | CGA | 728 |
|---|---|---|---|---|---|---|---|---|---|---|---|---|---|---|---|---|
| Glu | Gly | His | Asn | Asn | Thr | Asn | Lys | Val | Glu | Pro | His | Ala | Gly | Gln | Arg | |
| | 210 | | | | | 215 | | | | | 220 | | | | | |

| GCG | GTA | CTA | AAA | TAT | AAG | TTG | AAA | TTT | GAG | AAT | GGT | TTA | CAT | CAA | GGT | 776 |
|---|---|---|---|---|---|---|---|---|---|---|---|---|---|---|---|---|
| Ala | Val | Leu | Lys | Tyr | Lys | Leu | Lys | Phe | Glu | Asn | Gly | Leu | His | Gln | Gly | |
| 225 | | | | | 230 | | | | | 235 | | | | | 240 | |

| GAC | TAC | TTT | GAC | TTT | ACT | TTA | TCA | AAT | AAT | GTA | AAT | ACG | CAT | GGC | GTA | 824 |
|---|---|---|---|---|---|---|---|---|---|---|---|---|---|---|---|---|
| Asp | Tyr | Phe | Asp | Phe | Thr | Leu | Ser | Asn | Asn | Val | Asn | Thr | His | Gly | Val | |
| | | | | 245 | | | | | 250 | | | | | 255 | | |

| TCA | ACT | GCT | AGA | AAA | GTA | CCA | GAA | ATT | AAA | AAT | GGT | TCA | GTC | GTA | ATG | 872 |
|---|---|---|---|---|---|---|---|---|---|---|---|---|---|---|---|---|
| Ser | Thr | Ala | Arg | Lys | Val | Pro | Glu | Ile | Lys | Asn | Gly | Ser | Val | Val | Met | |
| | | | 260 | | | | | 265 | | | | | 270 | | | |

| GCG | ACA | GGT | GAA | GTT | TTA | GAA | GGT | GGA | AAG | ATT | AGA | TAT | ACA | TTT | ACA | 920 |
|---|---|---|---|---|---|---|---|---|---|---|---|---|---|---|---|---|
| Ala | Thr | Gly | Glu | Val | Leu | Glu | Gly | Gly | Lys | Ile | Arg | Tyr | Thr | Phe | Thr | |
| | | 275 | | | | | 280 | | | | | 285 | | | | |

| AAT | GAT | ATT | CAA | GAT | AAG | GTT | GAT | GTA | ACG | GCT | GAA | CTA | GAA | ATT | AAT | 968 |
|---|---|---|---|---|---|---|---|---|---|---|---|---|---|---|---|---|
| Asn | Asp | Ile | Gln | Asp | Lys | Val | Asp | Val | Thr | Ala | Glu | Leu | Glu | Ile | Asn | |
| | 290 | | | | | 295 | | | | | 300 | | | | | |

| TTA | TTT | ATT | GAT | CCT | AAA | ACT | GTA | CAA | ACT | AAT | GGA | AAT | CAA | ACT | ATA | 1016 |
|---|---|---|---|---|---|---|---|---|---|---|---|---|---|---|---|---|
| Leu | Phe | Ile | Asp | Pro | Lys | Thr | Val | Gln | Thr | Asn | Gly | Asn | Gln | Thr | Ile | |
| 305 | | | | | 310 | | | | | 315 | | | | | 320 | |

| ACT | TCA | ACA | CTA | AAT | GAA | GAA | CAA | ACT | TCA | AAG | GAA | TTA | GAT | GTT | AAA | 1064 |
|---|---|---|---|---|---|---|---|---|---|---|---|---|---|---|---|---|
| Thr | Ser | Thr | Leu | Asn | Glu | Glu | Gln | Thr | Ser | Lys | Glu | Leu | Asp | Val | Lys | |
| | | | | 325 | | | | | 330 | | | | | 335 | | |

| TAT | AAA | GAT | GGT | ATT | GGG | AAT | TAT | TAT | GCC | AAT | TTA | AAT | GGA | TCG | ATT | 1112 |
|---|---|---|---|---|---|---|---|---|---|---|---|---|---|---|---|---|
| Tyr | Lys | Asp | Gly | Ile | Gly | Asn | Tyr | Tyr | Ala | Asn | Leu | Asn | Gly | Ser | Ile | |
| | | | 340 | | | | | 345 | | | | | 350 | | | |

| GAG | ACA | TTT | AAT | AAA | GCG | AAT | AAT | AGA | TTT | TCG | CAT | GTT | GCA | TTT | ATT | 1160 |

|  |  |  |  |  |  |  |  |  |  |  |  |  |  |  |  |  |
|---|---|---|---|---|---|---|---|---|---|---|---|---|---|---|---|---|
| Glu | Thr | Phe | Asn | Lys | Ala | Asn | Asn | Arg | Phe | Ser | His | Val | Ala | Phe | Ile |  |
|  |  | 355 |  |  |  |  | 360 |  |  |  | 365 |  |  |  |  |  |
| AAA | CCT | AAT | AAT | GGT | AAA | ACG | ACA | AGT | GTG | ACT | GTT | ACT | GGA | ACT | TTA | 1208 |
| Lys | Pro | Asn | Asn | Gly | Lys | Thr | Thr | Ser | Val | Thr | Val | Thr | Gly | Thr | Leu |  |
|  | 370 |  |  |  | 375 |  |  |  |  | 380 |  |  |  |  |  |  |
| ATG | AAA | GGT | AGT | AAT | CAG | AAT | GGA | AAT | CAA | CCA | AAA | GTT | AGG | ATA | TTT | 1256 |
| Met | Lys | Gly | Ser | Asn | Gln | Asn | Gly | Asn | Gln | Pro | Lys | Val | Arg | Ile | Phe |  |
| 385 |  |  |  |  | 390 |  |  |  |  | 395 |  |  |  |  | 400 |  |
| GAA | TAC | TTG | GGT | AAT | AAT | GAA | GAC | ATA | GCG | AAG | AGT | GTA | TAT | GCA | AAT | 1304 |
| Glu | Tyr | Leu | Gly | Asn | Asn | Glu | Asp | Ile | Ala | Lys | Ser | Val | Tyr | Ala | Asn |  |
|  |  |  |  | 405 |  |  |  |  | 410 |  |  |  |  | 415 |  |  |
| ACG | ACA | GAT | ACT | TCT | AAA | TTT | AAA | GAA | GTC | ACA | AGT | AAT | ATG | AGT | GGG | 1352 |
| Thr | Thr | Asp | Thr | Ser | Lys | Phe | Lys | Glu | Val | Thr | Ser | Asn | Met | Ser | Gly |  |
|  |  |  | 420 |  |  |  |  | 425 |  |  |  |  | 430 |  |  |  |
| AAT | TTG | AAT | TTA | CAA | AAT | AAT | GGA | AGC | TAT | TCA | TTG | AAT | ATA | GAA | AAT | 1400 |
| Asn | Leu | Asn | Leu | Gln | Asn | Asn | Gly | Ser | Tyr | Ser | Leu | Asn | Ile | Glu | Asn |  |
|  |  | 435 |  |  |  |  | 440 |  |  |  |  | 445 |  |  |  |  |
| CTA | GAT | AAA | ACT | TAT | GTT | GTT | CAC | TAT | GAT | GGA | GAG | TAT | TTA | AAT | GGT | 1448 |
| Leu | Asp | Lys | Thr | Tyr | Val | Val | His | Tyr | Asp | Gly | Glu | Tyr | Leu | Asn | Gly |  |
|  | 450 |  |  |  |  | 455 |  |  |  |  | 460 |  |  |  |  |  |
| ACT | GAT | GAA | GTT | GAT | TTT | AGA | ACA | CAA | ATG | GTA | GGA | CAT | CCA | GAG | CAA | 1496 |
| Thr | Asp | Glu | Val | Asp | Phe | Arg | Thr | Gln | Met | Val | Gly | His | Pro | Glu | Gln |  |
| 465 |  |  |  |  | 470 |  |  |  |  | 475 |  |  |  |  | 480 |  |
| CTT | TAT | AAG | TAT | TAT | TAT | GAT | AGA | GGA | TAT | ACC | TTA | ACT | TGG | GAT | AAT | 1544 |
| Leu | Tyr | Lys | Tyr | Tyr | Tyr | Asp | Arg | Gly | Tyr | Thr | Leu | Thr | Trp | Asp | Asn |  |
|  |  |  |  | 485 |  |  |  |  | 490 |  |  |  |  | 495 |  |  |
| GGT | TTA | GTT | TTA | TAC | AGT | AAT | AAA | GCG | AAC | GGA | AAT | GAG | AAA | AAT | GGT | 1592 |
| Gly | Leu | Val | Leu | Tyr | Ser | Asn | Lys | Ala | Asn | Gly | Asn | Glu | Lys | Asn | Gly |  |
|  |  |  | 500 |  |  |  |  | 505 |  |  |  |  | 510 |  |  |  |
| CCG | ATT | ATT | CAA | AAT | AAT | AAA | TTT | GAA | TAT | AAA | GAA | GAT | ACA | ATT | AAA | 1640 |
| Pro | Ile | Ile | Gln | Asn | Asn | Lys | Phe | Glu | Tyr | Lys | Glu | Asp | Thr | Ile | Lys |  |
|  |  | 515 |  |  |  |  | 520 |  |  |  |  | 525 |  |  |  |  |
| GAA | ACT | CTT | ACA | GGT | CAA | TAT | GAT | AAG | AAT | TTA | GTA | ACT | ACT | GTT | GAA | 1688 |
| Glu | Thr | Leu | Thr | Gly | Gln | Tyr | Asp | Lys | Asn | Leu | Val | Thr | Thr | Val | Glu |  |
|  | 530 |  |  |  |  | 535 |  |  |  |  | 540 |  |  |  |  |  |
| GAG | GAA | TAT | GAT | TCA | TCA | ACT | CTT | GAC | ATT | GAT | TAC | CAC | ACA | GCT | ATA | 1736 |
| Glu | Glu | Tyr | Asp | Ser | Ser | Thr | Leu | Asp | Ile | Asp | Tyr | His | Thr | Ala | Ile |  |
| 545 |  |  |  |  | 550 |  |  |  |  | 555 |  |  |  |  | 560 |  |
| GAT | GGT | GGA | GGT | GGA | TAT | GTT | GAT | GGA | TAC | ATT | GAA | ACA | ATA | GAA | GAA | 1784 |
| Asp | Gly | Gly | Gly | Gly | Tyr | Val | Asp | Gly | Tyr | Ile | Glu | Thr | Ile | Glu | Glu |  |
|  |  |  |  | 565 |  |  |  |  | 570 |  |  |  |  | 575 |  |  |
| ACG | GAT | TCA | TCA | GCT | ATT | GAT | ATC | GAT | TAC | CAT | ACT | GCT | GTG | GAT | AGC | 1832 |
| Thr | Asp | Ser | Ser | Ala | Ile | Asp | Ile | Asp | Tyr | His | Thr | Ala | Val | Asp | Ser |  |
|  |  |  | 580 |  |  |  |  | 585 |  |  |  |  | 590 |  |  |  |
| GAA | GCA | GGT | CAC | GTT | GGA | GGA | TAC | ACT | GAG | TCC | TCT | GAG | GAA | TCA | AAT | 1880 |
| Glu | Ala | Gly | His | Val | Gly | Gly | Tyr | Thr | Glu | Ser | Ser | Glu | Glu | Ser | Asn |  |
|  |  | 595 |  |  |  |  | 600 |  |  |  |  | 605 |  |  |  |  |
| CCA | ATT | GAC | TTT | GAA | GAA | TCT | ACA | CAT | GAA | AAT | TCA | AAA | CAT | CAC | GCT | 1928 |
| Pro | Ile | Asp | Phe | Glu | Glu | Ser | Thr | His | Glu | Asn | Ser | Lys | His | His | Ala |  |
| 610 |  |  |  |  | 615 |  |  |  |  | 620 |  |  |  |  |  |  |
| GAT | GTT | GTT | GAA | TAT | GAA | GAA | GAT | ACA | AAC | CCA | GGT | GGT | GGT | CAG | GTT | 1976 |
| Asp | Val | Val | Glu | Tyr | Glu | Glu | Asp | Thr | Asn | Pro | Gly | Gly | Gly | Gln | Val |  |
| 625 |  |  |  |  | 630 |  |  |  |  | 635 |  |  |  |  | 640 |  |
| ACT | ACT | GAG | TCT | AAT | TTA | GTT | GAA | TTT | GAC | GAA | GAG | TCT | ACA | AAA | GGT | 2024 |
| Thr | Thr | Glu | Ser | Asn | Leu | Val | Glu | Phe | Asp | Glu | Glu | Ser | Thr | Lys | Gly |  |
|  |  |  |  | 645 |  |  |  |  | 650 |  |  |  |  | 655 |  |  |
| ATT | GTA | ACT | GGC | GCA | GTG | AGC | GAT | CAT | ACA | ACA | GTT | GAA | GAT | ACG | AAA | 2072 |
| Ile | Val | Thr | Gly | Ala | Val | Ser | Asp | His | Thr | Thr | Val | Glu | Asp | Thr | Lys |  |
|  |  |  | 660 |  |  |  |  | 665 |  |  |  |  | 670 |  |  |  |
| GAA | TAT | ACA | ACT | GAA | AGT | AAT | CTG | ATT | GAA | TTA | GTG | GAT | GAA | TTA | CCT | 2120 |

```
Glu Tyr Thr Thr Glu Ser Asn Leu Ile Glu Leu Val Asp Glu Leu Pro
        675                 680                 685

GAA GAG CAT GGT CAA GCA CAA GGA CCA GTC GAG GAA ATT ACT AAA AAC    2168
Glu Glu His Gly Gln Ala Gln Gly Pro Val Glu Glu Ile Thr Lys Asn
    690                 695                 700

AAT CAT CAT ATT TCT CAT TCT GGT TTA GGA ACT GAA AAT GGT CAC GGG    2216
Asn His His Ile Ser His Ser Gly Leu Gly Thr Glu Asn Gly His Gly
705                     710                 715                 720

AAT TAT GAC GTG ATT GAA GAA ATC GAA GAA AAT AGC CAC GTT GAT ATT    2264
Asn Tyr Asp Val Ile Glu Glu Ile Glu Glu Asn Ser His Val Asp Ile
            725                 730                 735

AAG AGT GAA TTA GGT TAT GAA GGT GGC CAA AAT AGC GGT AAC CAG TCA    2312
Lys Ser Glu Leu Gly Tyr Glu Gly Gly Gln Asn Ser Gly Asn Gln Ser
                740                 745                 750

TTC GAG GAA GAC ACA GAA GAA GAC AAA CCT AAA TAT GAA CAA GGT GGC    2360
Phe Glu Glu Asp Thr Glu Glu Asp Lys Pro Lys Tyr Glu Gln Gly Gly
        755                 760                 765

AAT ATC GTA GAT ATC GAT TTT GAT AGT GTA CCT CAA ATT CAT GGT CAA    2408
Asn Ile Val Asp Ile Asp Phe Asp Ser Val Pro Gln Ile His Gly Gln
770                 775                 780

AAT AAA GGT AAT CAG TCA TTC GAG GAA GAT ACA GAA AAA GAC AAA CCT    2456
Asn Lys Gly Asn Gln Ser Phe Glu Glu Asp Thr Glu Lys Asp Lys Pro
785                 790                 795                 800

AAG TAT GAA CAT GGC GGT AAC ATC ATT GAT ATC GAC TTC GAC AGT GTG    2504
Lys Tyr Glu His Gly Gly Asn Ile Ile Asp Ile Asp Phe Asp Ser Val
            805                 810                 815

CCA CAT ATT CAC GGA TTC AAT AAG CAC ACT GAA ATT ATT GAA GAA GAT    2552
Pro His Ile His Gly Phe Asn Lys His Thr Glu Ile Ile Glu Glu Asp
                820                 825                 830

ACA AAT AAA GAT AAA CCA AGT TAT CAA TTC GGT GGA CAC AAT AGT GTT    2600
Thr Asn Lys Asp Lys Pro Ser Tyr Gln Phe Gly Gly His Asn Ser Val
        835                 840                 845

GAC TTT GAA GAA GAT ACA CTT CCA AAA GTA AGC GGC CAA AAT GAA GGT    2648
Asp Phe Glu Glu Asp Thr Leu Pro Lys Val Ser Gly Gln Asn Glu Gly
850                 855                 860

CAA CAA ACG ATT GAA GAA GAT ACA ACA CCT CCA ATC GTG CCA CCA ACG    2696
Gln Gln Thr Ile Glu Glu Asp Thr Thr Pro Pro Ile Val Pro Pro Thr
865                 870                 875                 880

CCA CCG ACA CCA GAA GTA CCA AGT GAG CCG GAA ACA CCA ACG CCA CCA    2744
Pro Pro Thr Pro Glu Val Pro Ser Glu Pro Glu Thr Pro Thr Pro Pro
            885                 890                 895

ACA CCA GAA GTA CCA AGT GAG CCG GAA ACA CCA ACA CCA CCG ACA CCA    2792
Thr Pro Glu Val Pro Ser Glu Pro Glu Thr Pro Thr Pro Pro Thr Pro
                900                 905                 910

GAA GTG CCG AGT GAG CCA GAA ACT CCA ACA CCG CCA ACA CCA GAG GTA    2840
Glu Val Pro Ser Glu Pro Glu Thr Pro Thr Pro Pro Thr Pro Glu Val
        915                 920                 925

CCA GCT GAA CCT GGT AAA CCA GTA CCA CCT GCC AAA GAA GAA CCT AAA    2888
Pro Ala Glu Pro Gly Lys Pro Val Pro Pro Ala Lys Glu Glu Pro Lys
930                 935                 940

AAG CCT TCT AAA CCA GTG GAA CAA GGT AAA GTA GTA ACA CCT GTT ATT    2936
Lys Pro Ser Lys Pro Val Glu Gln Gly Lys Val Val Thr Pro Val Ile
945                 950                 955                 960

GAA ATC AAT GAA AAG GTT AAA GCA GTG GCA CCA ACT AAA AAA CCA CAA    2984
Glu Ile Asn Glu Lys Val Lys Ala Val Ala Pro Thr Lys Lys Pro Gln
            965                 970                 975

TCT AAG AAA TCT GAA CTA CCT GAA ACA GGT GGA GAA GAA TCA ACA AAC    3032
Ser Lys Lys Ser Glu Leu Pro Glu Thr Gly Gly Glu Glu Ser Thr Asn
                980                 985                 990

AAA GGT ATG TTG TTC GGC GGA TTA TTC AGC ATT CTA GGT TTA GCA TTA    3080
```

```
Lys Gly Met Leu Phe Gly Gly Leu Phe Ser Ile Leu Gly Leu Ala Leu
        995                 1000                1005

TTA CGC AGA AAT AAA AAG AAT CAC AAA GCA TAA T AAACAAAAAT                    3124
Leu Arg Arg Asn Lys Lys Asn His Lys Ala  *
    1010                 1015

TGACGGGTTT ATTTCATAAA TTATATGAAG TAAGCCTGTT TTTTTATATT AAATCAAATT           3184

TCTAATAGAA AATTAGAGTG TTTTCTGATT GCTTCATTGG TTTATGTCTG ATGATTGATA           3244

ACGAACTGAG AGATAAAGTT AGAATTTTAA AGTAGT                                    3280
```